US008986277B2

(12) United States Patent
Yokoyama

(10) Patent No.: US 8,986,277 B2
(45) **Date of Patent: *Mar. 24, 2015**

(54) CONNECTOR, SYRINGE ASSEMBLY, AND CONNECTOR FOR MIXING

(71) Applicant: Terumo Kabushiki Kaisha, Shibuya-ku (JP)

(72) Inventor: Kenji Yokoyama, Ashigarakamigun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/941,140

(22) Filed: Jul. 12, 2013

(65) Prior Publication Data

US 2013/0296822 A1 Nov. 7, 2013

Related U.S. Application Data

(60) Division of application No. 13/112,332, filed on May 20, 2011, now Pat. No. 8,512,308, which is a continuation of application No. PCT/JP2009/069600, filed on Nov. 19, 2009.

(30) Foreign Application Priority Data

Nov. 21, 2008 (JP) ................................ 2008-298428

(51) Int. Cl.
*A61B 19/00* (2006.01)
*A61M 5/32* (2006.01)
(Continued)

(52) U.S. Cl.
CPC *A61J 1/2096* (2013.01); *A61J 1/16* (2013.01); *A61J 2001/2013* (2013.01); *A61J 2001/2055* (2013.01); *A61J 2001/2058* (2013.01); *A61J 2001/2065* (2013.01)
USPC ............................ 604/413; 604/403; 604/411

(58) Field of Classification Search
None
See application file for complete search history.

(56) References Cited

U.S. PATENT DOCUMENTS 4,564,054 A * 1/1986 Gustavsson .................. 141/329
5,466,220 A * 11/1995 Brenneman .................... 604/87
(Continued)

FOREIGN PATENT DOCUMENTS

JP 9-187488 A 7/1997
JP 2984642 B2 11/1999
(Continued)

OTHER PUBLICATIONS

International Search Report (PCT/ISA/210) issued on Dec. 15, 2009, by Japanese Patent Office as the International Searching Authority for International Application No. PCT/JP2009/069600.

*Primary Examiner* — Tan-Uyen (Jackie) T Ho
*Assistant Examiner* — Eric Bryant
(74) *Attorney, Agent, or Firm* — Buchanan Ingersoll & Rooney PC

(57) ABSTRACT

A connector is configured to be connected to a syringe assembly provided with at least one syringe having an outer cylinder with a protruding tube-shaped port, and a holder which holds the syringe. The connector includes a connector main body mountable on a container containing a medical solution; a tube-shaped fitting section protruding from the upper section of the connector main body for receiving the syringe to connect the inside of the syringe and the inside of the container when the syringe port is fitted in the fitting section; and fixing means having a lock mechanism that fixes the syringe assembly to the connector main body when the syringe port is fitted in the fitting section, an operating section to release the fixed state provided by the lock mechanism, and a push-out section that pushes out the syringe assembly when the fixing releasing operation is performed.

8 Claims, 19 Drawing Sheets

(51) Int. Cl.
*A61J 1/20* (2006.01)
*A61J 1/16* (2006.01)

(56) References Cited

U.S. PATENT DOCUMENTS

| | | | | |
|---|---|---|---|---|
| 5,839,715 | A | 11/1998 | Leinsing | |
| 6,471,670 | B1 | 10/2002 | Enrenfels et al. | |
| 6,474,375 | B2 * | 11/2002 | Spero et al. | 141/329 |
| 6,645,181 | B1 * | 11/2003 | Lavi et al. | 604/191 |
| 2001/0025671 | A1 | 10/2001 | Safabash | |
| 2004/0044327 | A1 | 3/2004 | Hasegawa | |
| 2006/0184013 | A1 * | 8/2006 | Emanuel et al. | 600/426 |
| 2009/0038701 | A1 * | 2/2009 | Delmotte | 137/896 |
| 2009/0204066 | A1 * | 8/2009 | Radmer et al. | 604/86 |

FOREIGN PATENT DOCUMENTS

| | | | |
|---|---|---|---|
| JP | 2004-097253 | A | 4/2004 |
| JP | 2004-522541 | A | 7/2004 |
| JP | 2005-278924 | A | 10/2005 |

* cited by examiner

CONNECTOR, SYRINGE ASSEMBLY, AND CONNECTOR FOR MIXING

RELATED APPLICATIONS

This application is a divisional of application Ser. No. 13/112,332, filed May 20, 2011, which is a continuation of International Application No. PCT/JP2009/069600 filed on Nov. 19, 2009 and claims priority to Japanese Patent Application No. 2008-298428 filed in on Nov. 21, 2008, the entire content of each of which is incorporated herein by reference.

TECHNOLOGICAL FIELD

The present disclosure generally relates to a connector. More specifically, the disclosure involves a connector used to connect a syringe to a container containing a medical solution to allow the syringe to draw the medical solution out of the container.

BACKGROUND INFORMATION

In medical facilities, to perform drop injection into a patient, or to administer an anti-adhesive material, a living tissue adhesive or the like into a patient, or the like, a medical solution may be used by drawing the solution from a medical solution container in which it is contained through use of a syringe. In such a situation, the medical solution container and the syringe are interconnected through a connector. An example of a connector is disclosed in Japanese Patent Laid-Open No. 2004-97253.

The connector described in this document includes a tube-like fitting section for having a port of a syringe fitted therein, and a needle which communicates with the fitting section and pierces a rubber stopper mounted to a port of the medical solution container. The connector thus configured is used by piercing the rubber stopper of the medical solution container with the needle to connect the connector with the solution container. In this condition, the port of the syringe is fitted into the fitting section so as to load the syringe with the medical solution.

In the connector, however, the connection with the port of the syringe is based on the fitting structure, so that the problem of difficult disconnection of the syringe from the connector can arise when the fitting is unsatisfactory, for example. Besides, in the case where the fitting force is excessively high in magnitude, an attempt to disconnect the syringe from the connector may be followed by a situation in which the disconnection is very difficult or impossible to achieve.

SUMMARY

The connector disclosed here is adapted to be connected to a syringe assembly provided with at least one syringe having an outer cylinder with a tube-shaped port protruding from a leading end section, and a holder which holds the syringe. The connector includes: a connector main body mountable to a medical solution container containing a medical solution; a tube-shaped fitting section which protrudes from an upper section of the connector main body, is adapted to receive the port of the syringe fitted therein, and to communicate the inside of the syringe and the inside of the medical solution container with each other when the port of the syringe is fitted in the fitting section; a lock mechanism that fixes the syringe assembly to the connector main body when the port of the syringe is fitted in the fitting section; an operating section that performs a fixing releasing operation of resetting a fixed state provided by the lock mechanism, and a push-out section that pushes out the syringe assembly toward a base end in an interlocked manner with the fixing releasing operation when the fixing releasing operation is performed.

In the connector disclosed here, the fitting between the port of the syringe and the fitting section is preferably released by pushing-out by the push-out section.

The lock mechanism has a pair of clamp pieces which clamp the holder therebetween and are engaged with the holder, and a biasing section by which the pair of clamp pieces are biased toward each other. In addition, the biasing section is preferably composed of a spring (leaf spring) bridgingly provided between the pair of clamp pieces.

The operating section is composed of pressing pieces which are provided correspondingly on the clamp pieces and which perform a pressing operation of pressing the clamp pieces away from each other. The push-out section is preferably composed of projections projecting inwardly from intermediate portions in the longitudinal directions of the clamp pieces. The push-out section makes contact with the holder in the fixed state, and presses the holder when the fixing releasing operation is performed.

The medical solution container has a bottomed cylinder-like container main body, and a stopper formed from an elastic material for stopping up an aperture of the container main body, and the connector main body is provided with a needle pipe for piercing the stopper, the needle pipe communicating with the fitting section and projecting toward the side opposite to the fitting section.

The releasing of the fixed state and the pushing-out by the push-out section are performed substantially simultaneously. The pair of clamp pieces and the biasing section are preferably formed integrally.

The connector main body can be tube-shaped, and the pressing pieces can be disposed symmetrically about a center axis of the connector main body.

In addition, the outer peripheral portion of the port can have a tapered shape with an outside diameter gradually decreasing toward the leading end of the port, and the inner peripheral portion of the fitting section has a tapered shape corresponding to the shape of the port.

The syringe assembly preferably has two syringes held in parallel to each other by the holder, and two fitting sections are disposed in parallel so as to correspond to the syringes. The lock mechanism is preferably disposed between the two fitting sections.

The fitting section has a function of positioning the syringe assembly relative to the connector main body.

The connector disclosed here is connectable to a syringe assembly quite assuredly, and the connected syringe assembly can be disconnected rather easily and assuredly through a relatively easy operation.

In accordance with another aspect, a connector to be connected to the syringe assembly includes a connector main body mountable on a medical solution container possessing an interior containing a medical solution, a needle pipe projecting from a lower section of the container main body, with the needle pipe possessing a sharp needle point at its distal end, the needle pipe including a lumen opening to the sharp needle point, a tubular fitting protruding from an upper section of the connector main body to receive the port of the syringe, wherein the tubular fitting possesses an interior communicating with the lumen of the needle pipe, an arm rotatably mounted on the connector main body to engage the holder and hold the syringe assembly in place, an operating portion connected to the arm and operable by a user to move the arm out of engagement with the holder to release the syringe assembly, and a holding device connected to the arm to hold the arm in engagement with the holder until the operating portion is operated.

Another aspect of the disclosure here involves a mixing connector connectable to both a medicine container, which contains medicine and which is positioned in a first port of a holder, and a liquid container, which contains liquid different from the medicine and which is positioned in a second port of the holder possessing a configuration different from the configuration of the first port. The mixing connector comprises: a support section; a first tube-shaped section fixed to the support section, and a second tube-shaped section fixed to the support section. A double-pointed needle is supported in the support section and extends over a longitudinal extent, wherein the double-pointed needle includes a first portion projecting away from the support section in a first projecting direction and terminating at a sharpened end for puncturing a stopper in the medicine container, and wherein the double-pointed needle includes a second portion projecting away from the support section in a second projecting direction and terminating at a sharpened end for puncturing a stopper in the liquid container. The double-pointed needle possesses a lumen extending throughout the longitudinal extent of the double-pointed needle and opens to both the first sharpened end and the second sharpened end of the double-pointed needle. The first tube-shaped section projects away from the support section in the first projecting direction, and surrounds the first portion of the double-pointed needle so that a space exists between the outer peripheral surface of the first portion of the double-pointed needle and the inner peripheral surface of the first tube-shaped section. The second tube-shaped section projects away from the support section in the second projecting direction, and surrounds the second portion of the double-pointed needle so that a space exists between the outer peripheral surface of the second portion of the double-pointed needle and the inner peripheral surface of the second tube-shaped section. The first tube-shaped section and the second tube-shaped section each possess an outer periphery, with the outer periphery of the first tube-shaped section and the second tube-shaped section being differently shaped. The shape of the outer periphery of the first tube-shaped section permits the first tube-shaped section to be positioned in the first port of the holder and prevents the first tube-shaped section from being positioned in the second port of the holder, and the shape of the outer periphery of the second tube-shaped section permits the second tube-shaped section to be positioned in the second port of the holder and prevents the second tube-shaped section from being positioned in the first port of the holder.

Another aspect of the disclosure here involves a syringe assembly in combination with a connector. The syringe assembly comprises a syringe that includes a plunger slidably positioned in an outer cylinder, a tube-shaped port protruding from a leading end of the outer cylinder, and a holder fixed to the syringe, the holder including an engagement portion. The connector comprises: a connector main body configured to be mounted on a medical solution container containing a medical solution; a needle pipe projecting in a first projecting direction from the connector main body, with needle pipe including a sharp needle point at the end remote from the connector main body and a lumen opening to the sharp needle point. A tube-shaped fitting protrudes from the connector main body in a second projecting direction opposite the first projecting direction, and the tube-shaped fitting possessing an interior sized and shaped to receive the tube-shaped port of the syringe, wherein the interior of the tube-shaped fitting communicates with the lumen of the needle pipe. An arm is rotatably mounted on the connector main body to engage the engagement portion of the holder to fix the syringe assembly in place relative to the connector with the tube-shaped port of the syringe positioned in the tube-shaped fitting of the connector. A holding device is connected to the arm to hold the arm in engagement with the engagement portion of the holder and to permit the arm to be moved out of engagement with the engagement portion of the holder to permit the syringe assembly to be released from the connector.

BRIEF DESCRIPTION OF THE DRAWING FIGURES

Figure 19:
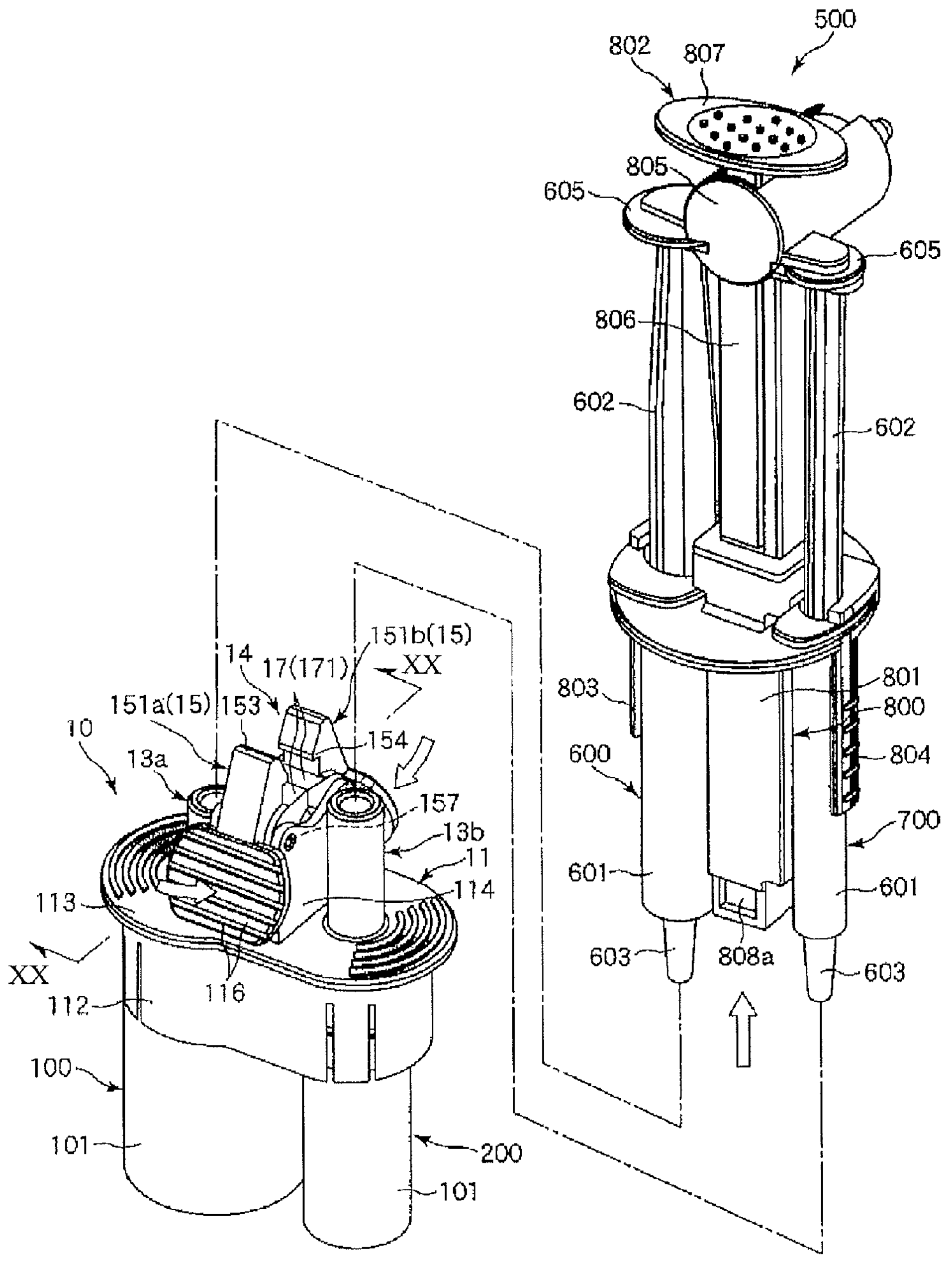
FIG. 19 is a view for describing sequentially the method of using the connector shown in FIG. 1.
Figure 20:
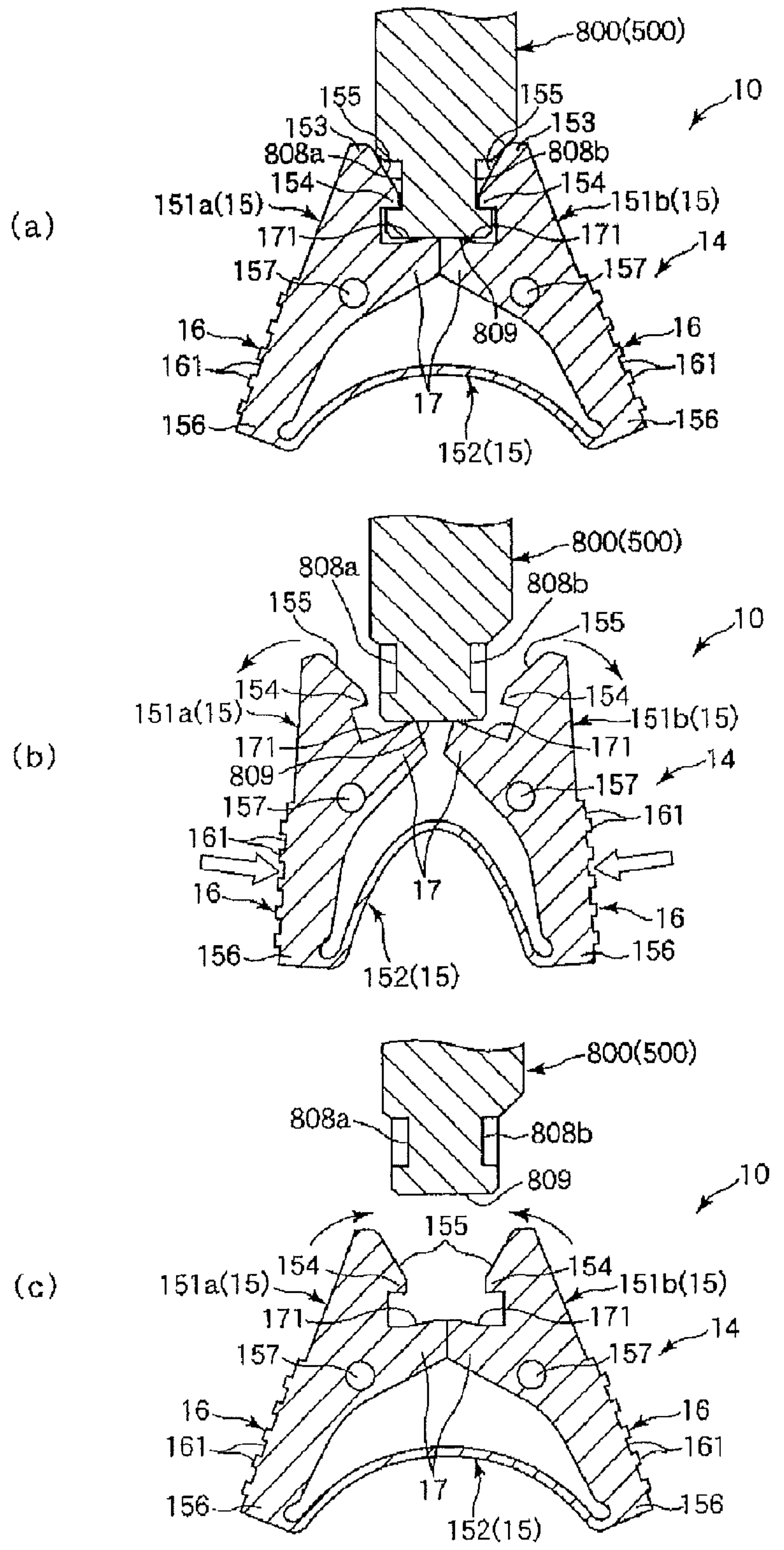

FIGS. 20(*a*)-20(*c*) are cross-sectional sectional views taken along the section line XX-XX in FIG. 19.

DETAILED DESCRIPTION

In the following description of the connector disclosed here, for convenience of description, the upper side in FIGS. 1 to 9 and FIGS. 12 to 20 is referred to as "upper" or "upper side," and the lower side is referred to as "lower" or "lower side." In addition, in FIG. 2, fixing means possessed by the connector according to the present disclosure is omitted, and, in FIG. 3, the fixing means possessed by the connector is drawn.

Figure 18:
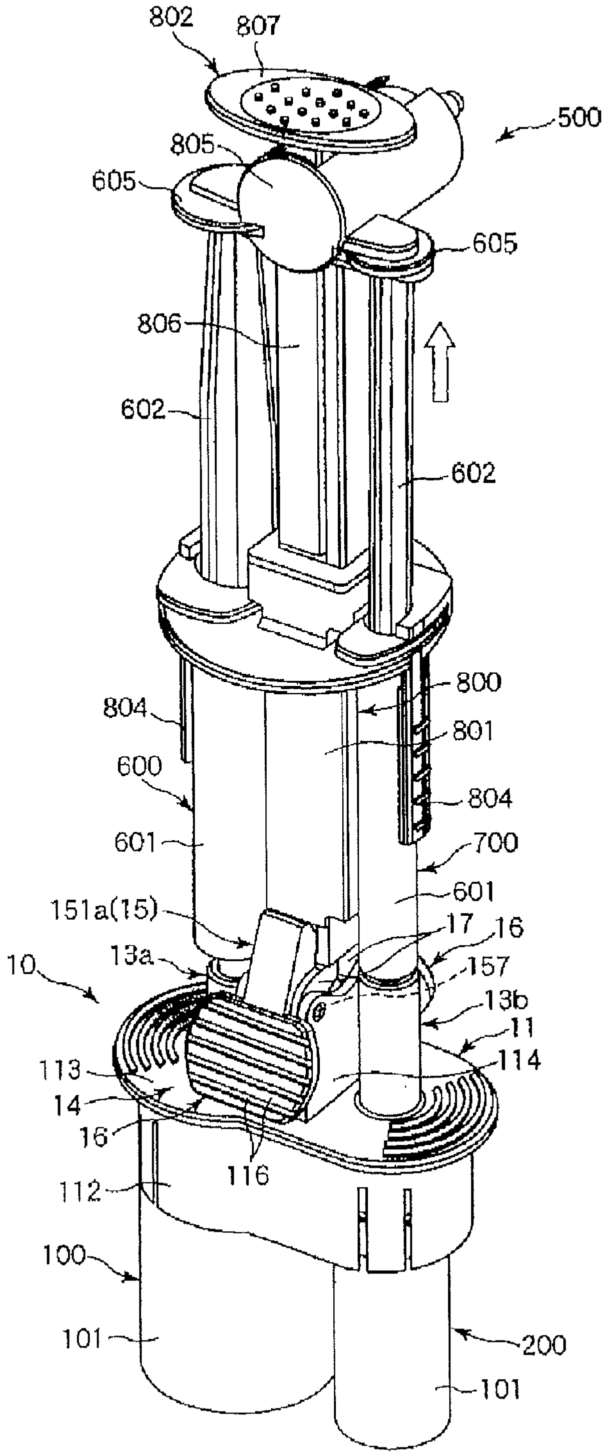
FIG. 18 is a view for describing sequentially the method of using the connector shown in FIG. 1.

The connector 10 is used in the context of being connected to a syringe assembly 500 at the time when, for example, prepared medical solutions are sucked or drawn from a first medicine container 100 and a second medicine container 200, which are filled with the medical solutions, into a first syringe 600 and a second syringe 700 of the syringe assembly 500, respectively (see FIG. 18).

Prior to description of the connector 10, a medical instrument set 1 in which the first medicine container 100 and the second medicine container 200 are to be held and the syringe assembly 500 will be described.

Figure 4:
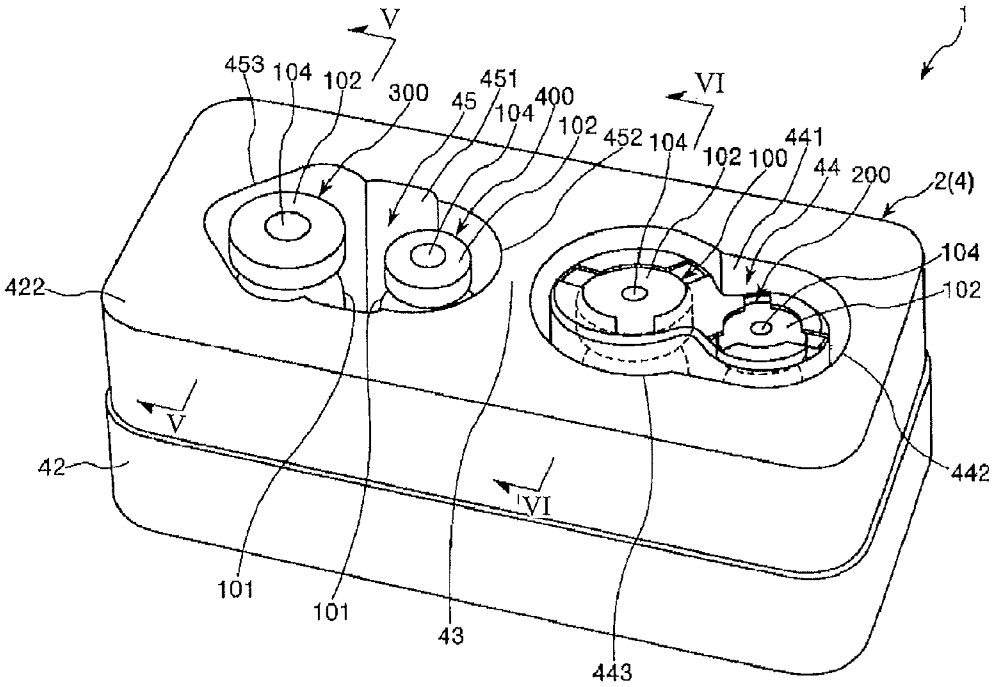
FIG. 4 is a perspective view of a medical container holder of a medical instrument set.
Figure 9:
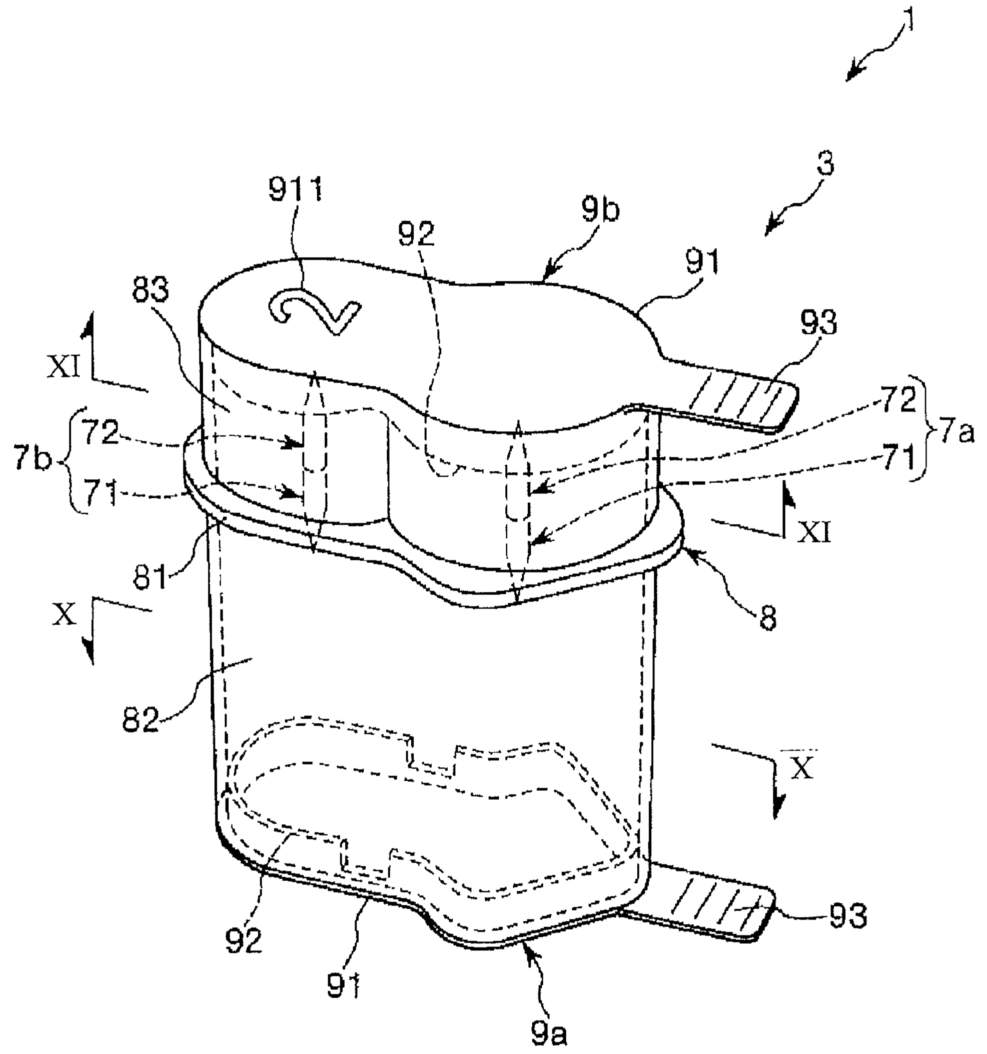
FIG. 9 is a perspective view of a connector (connector for mixing) of the medical instrument set.

As shown in FIGS. 4 and 9, the medical instrument set 1 includes a medical container holder 2 (hereinafter referred to simply as "holder") in which the first medicine container 100, the second medicine container 200, a first liquid container 300 and a second liquid container 400 are to be contained and held, and a connector for mixing (mixing connector) 3 which connects the first medicine container 100 and the first liquid container 300 to each other and connects the second medicine container 200 and the second liquid container 400 to each other.

Prior to description of each component of the medical instrument set 1, a description will first be set forth of the first medicine container 100, the second medicine container 200, the first liquid container 300 and the second liquid container 400.

The first medicine container 100, the second medicine container 200, the first liquid container 300 and the second liquid container 400 can be in the form of, for example, vials and the like, though the containers are not limited in that regard.

In the first medicine container 100 and the second medicine container 200, medicines are correspondingly contained.

The form or type of medicines is not particularly restricted, and examples include solid (tablets, granules, etc.), powder, and liquid. The medicine contained in the first medicine container 100 and the medicine contained in the second medicine container 200 are different from each other in kind, and are appropriately selected according to the uses of medical solutions prepared by dissolving the medicines in liquids, the purpose of use, the case, or the like. For example, in the case where the medical solution is a living tissue adhesive, one of the medicines may be thrombin and the other may be fibrinogen. By this, dispensing can be achieved. In the case where the medical solution is an antiadhesive material, one of the medicines may be carboxymethyldextrin modified by succinimidyl group, and the other may be a mixture of sodium hydrogencarbonate and sodium carbonate.

In addition, the inside of the first medicine container 100 and the inside of the second medicine container 200 are both kept at negative pressures.

On the other hand, the first liquid container 300 and the second liquid container 400 contain, liquids, for example, distilled water or the like, for diluting or dissolving the medicines. The liquid contained in the first liquid container 300 and the liquid contained in the second liquid container 400 may be of the same kind or of different kinds.

Now, the configuration of the first medicine container 100, the second medicine container 200, the first liquid container 300 and the second liquid container 400 will be described below, referring to an example where vials are used as these containers. Since these containers (particularly, the first medicine container 100 and the second medicine container 200, and the first liquid container 300 and the second liquid container 400) are substantially the same in configuration except for shape, the first medicine container 100 will be described representatively, it being understood that this description also applies to the other containers.

Figure 6:
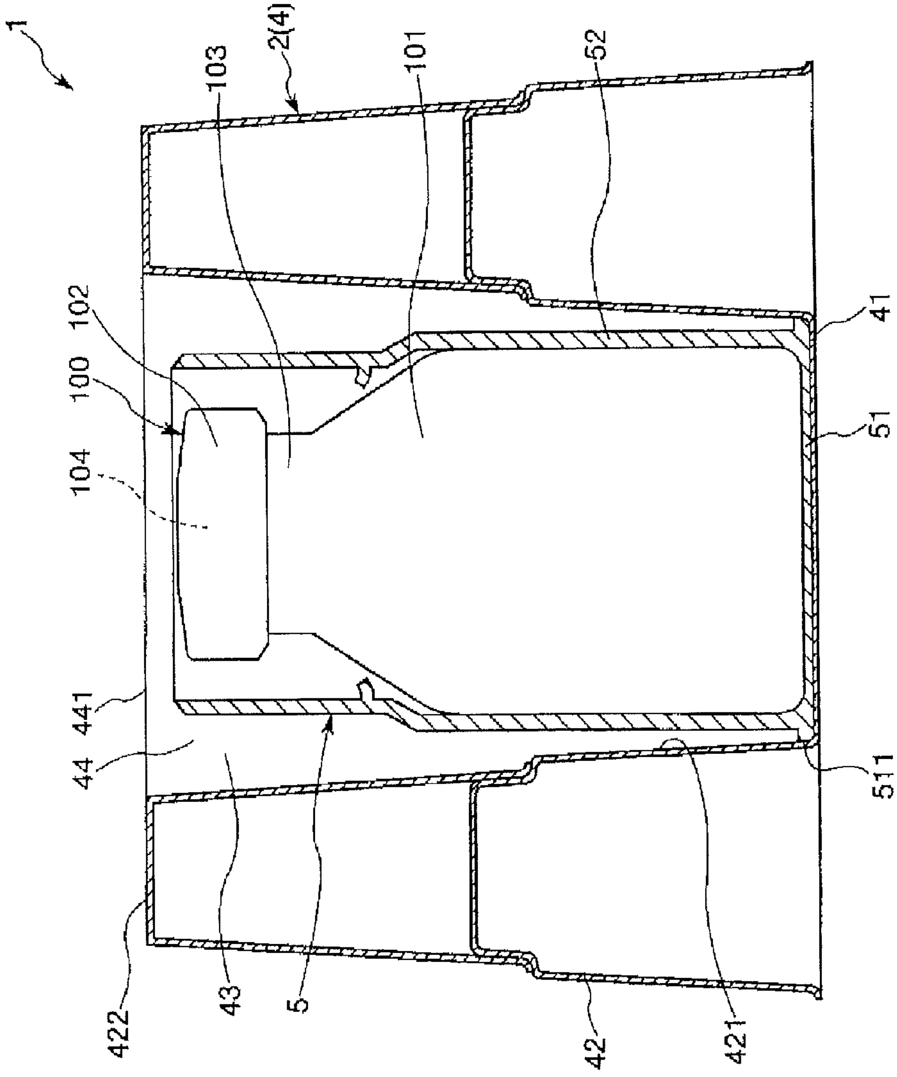
FIG. 6 is a sectional view taken along the section line VI-VI in FIG. 4.

As shown in FIG. 6, the first medicine container 100 has a hard bottle main body 101 having a bottomed tube-like shape. The bottle main body 101 has, on its upper side, a port section 102 formed with a port section aperture. A neck section 103 is positioned intermediately and is the section smallest in size in outside diameter. In the port section 102 is mounted a stopper or closure 104 with which the port section aperture is stopped up (closed) in a gas-tight manner.

The material constituting the bottle main body 101 is not particularly limited. Examples of the material include various glasses and various resins such as polyvinyl chloride, polyethylene, polypropylene, cyclic polyolefins, polystyrene, poly-(4-methylpentene-1), polycarbonate, acrylic resins, acrylonitrile-butadiene-styrene copolymer, polyesters such as polyethylene terephthalate, polyethylene naphthalate, etc., butadiene-styrene copolymer, and polyamides (e.g., 6-nylon, 6,6-nylon, 6,10-nylon, 12-nylon). Resins are more preferable than glasses. Where the bottle main body 101 is formed of a resin, it can be disposed of by incineration, so that the disposal is made less troublesome. The bottle main body 101 is preferably light-transmitting (substantially transparent or semi-transparent), for securing visibility of the inside of the bottle main body.

The stopper 104 is capable of being pierced by a needle such as a first double-pointed needle 7*a* or a second double-pointed needle 7*b* of the connector for mixing 3 (shown in FIG. 9). The material constituting the stopper 104 is not particularly limited. Examples of the material include elastic materials such as various rubber materials such as natural rubber, butyl rubber, isoprene rubber, butadiene rubber, styrene-butadiene rubber, silicone rubbers, etc., various thermoplastic elastomers based on polyurethane, polyester, polyamide, olefin, styrene or the like, and mixtures of them.

Here, the first medicine container 100 and the second medicine container 200 possess different shapes. In this embodiment, the internal volume of the first medicine container 100 is larger than that of the second medicine container 200. Specifically, the first medicine container 100 is greater than the second medicine container 200 in length in the longitudinal direction of container (bottle main body 101), in outside diameters of the bottle main body 101, the port section 102 and the neck section 103, and in inside diameter of the bottle main body 101.

In addition, the first liquid container 300 and the second liquid container 400 are different from each other in shape. In this embodiment, the internal volume of the first liquid container 300 is larger than that of the second liquid container 400. Specifically, the first liquid container 300 is greater than the second liquid container 400 in length in the longitudinal direction of container (bottle main body 101), in outside diameter of the bottle main body 101, the port section 102 and the neck section 103, and in inside diameter of the bottle main body 101.

The holder 2 can be mounted on a support base such as, for example, a table during use. As shown in FIG. 4, the holder 2 can hold the first medicine container 100 and the second medicine container 200 collectively, and can hold the first liquid container 300 and the second liquid container 400 collectively. The holder 2 includes a holder main body 4, a medicine-side loading member 5 to be loaded with the first medicine container 100 and the second medicine container 200, and a liquid-side loading member 6 to be loaded with the first liquid container 300 and the second liquid container 400.

Figure 5:
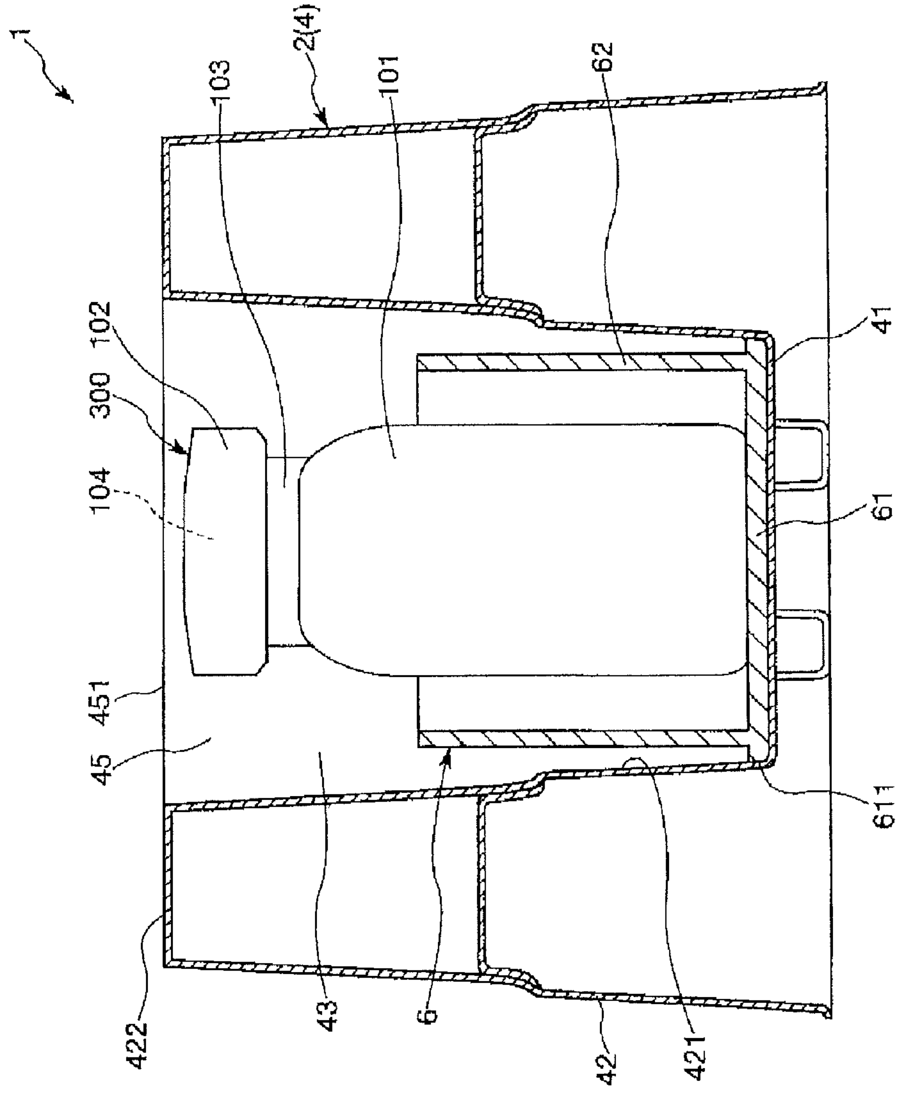
FIG. 5 is a cross-sectional view taken along the section line V-V in FIG. 4.

As shown in FIGS. 4 to 6, the holder main body 4 is composed of box-shaped members. Specifically, the holder main body 4 includes a bottom plate 41 and a side wall 42 so formed as to surround the bottom plate 41. In addition, the holder main body 4 has a partition section 43 with which the space surrounded by the bottom plate 41 and the side wall 42 is partitioned into two spaces. One of the two spaces formed by partitioning with the partition section 43 functions as a medicine-side containing section 44 in which the first medicine container 100 and the second medicine container 200 are contained in a juxtaposed manner, and the other of the two spaces functions as a liquid-side containing section 45 in which the first liquid container 300 and the second liquid container 400 are contained in a juxtaposed manner. While the side wall 42 is hollow in the illustrated embodiment shown in FIGS. 5 and 6, this configuration is not limitative, and the side wall 42 may be solid.

In the medicine-side containing section 44, the first medicine container 100 and the second medicine container 200 are vertically oriented such that their port sections 102 are located vertically above the main body 101.

In the liquid-side containing section 45, also, the first liquid container 300 and the second liquid container 400 are vertically oriented such that their port sections 102 are located vertically above the main body 101, in the same manner as the first medicine container 100 and the second medicine container 200 contained in the medicine-side containing section 44.

The material constituting the holder main body 4 is not limited to a specific material. Examples of the material include various flexible or rigid resins such as polyvinyl chloride, polyethylene, polypropylene, cyclic polyolefins, polystyrene, poly(4-methylpentene-1), polycarbonate, acrylic resins, acrylonitrile-butadiene-styrene copolymer, polyesters such as polyethylene terephthalate, polyethylene naphthalate, etc., butadiene-styrene copolymer, polyamides (e.g., 6-nylon, 6,6-nylon, 6,10-nylon, 12-nylon), etc., various metallic materials such as stainless steel, aluminum, copper, copper alloys, etc., various glasses, and various ceramics such as alumina, silica, etc.

As shown in FIG. 6, the medicine-side loading member 5 is contained in the medicine-side containing section 44 of the holder main body 4, together with the first medicine container 100 and the second medicine container 200. The medicine-side loading member 5 is to be loaded with the first medicine container 100 and the second medicine container 200.

Figure 8:
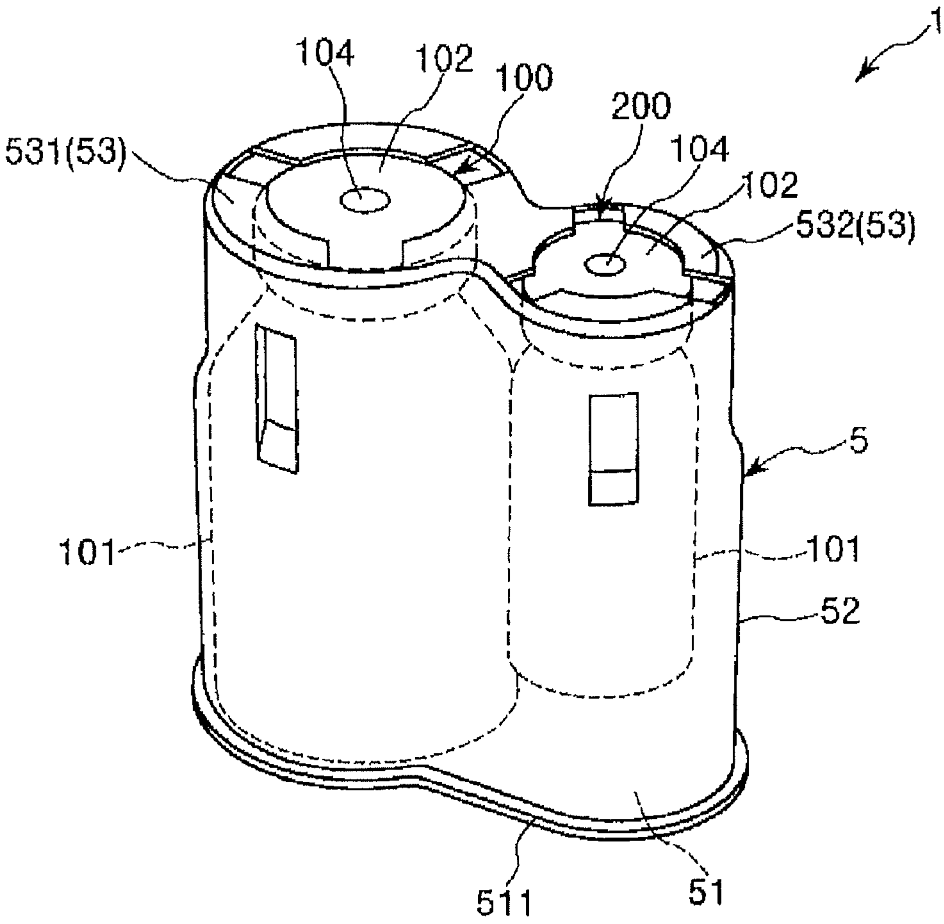
FIG. 8 is a perspective view of the medicine-side loading member of the medical container holder shown in FIG. 4 loaded with a medicine container.

As shown in FIG. 8, the medicine-side loading member 5 includes a bottom section 51, an upstanding wall section 52 extending upwardly from the bottom section 51, and a cap section 53.

The bottom section 51 is a section possessing a plan-view shape which conforms to the shape (daruma-shape, gourd-shape) of a medicine-side insertion port 441 of the medicine-side containing section 44 of the holder main body 4 which will be described later. In addition, the bottom section 51 supports the bottom portions of the medicine containers 110, 200 so that height of the port section 102 of the first medicine container 100 and the height of the port section 102 of the second medicine container 200 are substantially the same (i.e., the top of the port sections 102 of the two containers is at the same vertical position). This helps ensure that when the stoppers 104 press fitted into the port sections 102 are disinfected by use of adsorbent cotton impregnated with a disinfectant, for example, the stoppers 104 can be disinfected all together by the adsorbent cotton, so that the disinfecting operation can be carried out rather easily.

The wall section 52 is integrally formed in one piece with the bottom section 51. The wall section 52 is curved along an edge portion of the bottom section 51.

The cap section 53 shown in FIG. 8 is detachably attached to the upper portion of the wall section 52. The cap section 53 has: an annular first ring section 531 supporting the outer peripheral portion of the port section 102 of the first medicine container 100 loaded in the medicine-side leading member 5, in the state wherein the cap section 53 is attached to the wall section 52; and an annular second ring section 532 supporting the outer peripheral portion of the port section 102 of the second medicine container 200, in the attached state.

Figure 15:
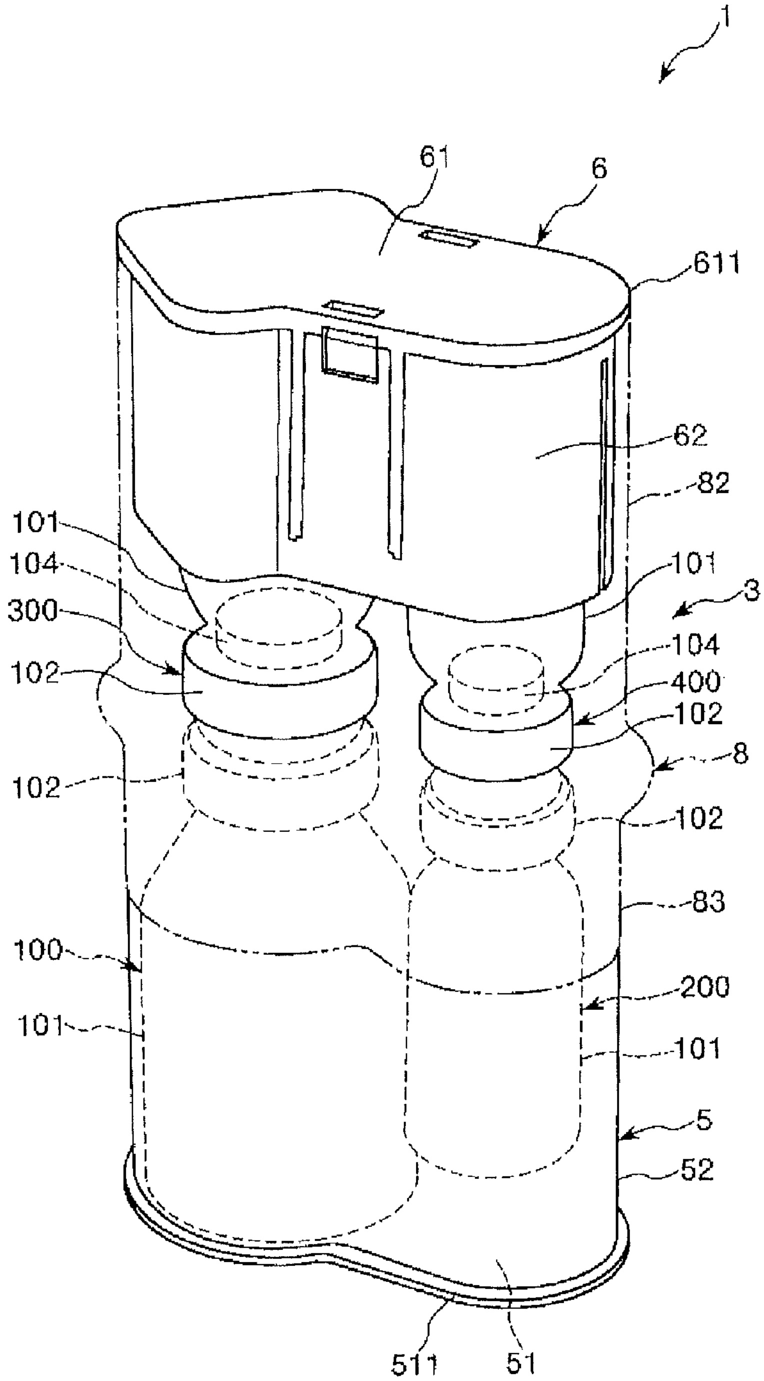
FIG. 15 is a view for describing sequentially the method of using the connector shown in FIG. 1.

In the medicine-side loading member 5 thus configured, the first medicine container 100 and the second medicine container 200 are collectively held. In addition, as shown in FIG. 15, the first medicine container 100 and the second medicine container 200 held in the medicine-side loading member 5 can be taken out of the holder main body 4 together with the medicine-side leading member 5. This helps ensure that even upon taking-out the first medicine container 100 and the second medicine container 200 from the holder main body 4, the positional relationship between the two medicine containers 100, 200 is maintained. Consequently, an operation of connecting a first syringe 600 to the first medicine container 100 and connecting a second syringe 700 to the second medicine container 200 can be carried out relatively assuredly.

As shown in FIGS. 6 and 8, the bottom section 51 has an edge portion protruding outwardly beyond the upstanding wall section 52. As shown in FIG. 6, this edge portion functions as an engaging portion 511 for engagement with a lower portion of an inner surface 421 of the side wall 42 defining the medicine-side containing section 44 of the holder main body 4. The engagement of the engaging portion 511 of the medicine-side loading member 5 with the side wall 42 of the holder main body 4 helps ensure that the medicine-side loading member 5 can be rather assuredly fixed to the holder main body 4. Consequently, even if the holder 2 is inverted upside down, the medicine-side loading member 5 as well as the first medicine container 100 and the second medicine container 200 held in the medicine-side loading member 5 can be inhibited or prevented from falling out of the holder main body 4.

Figure 14:
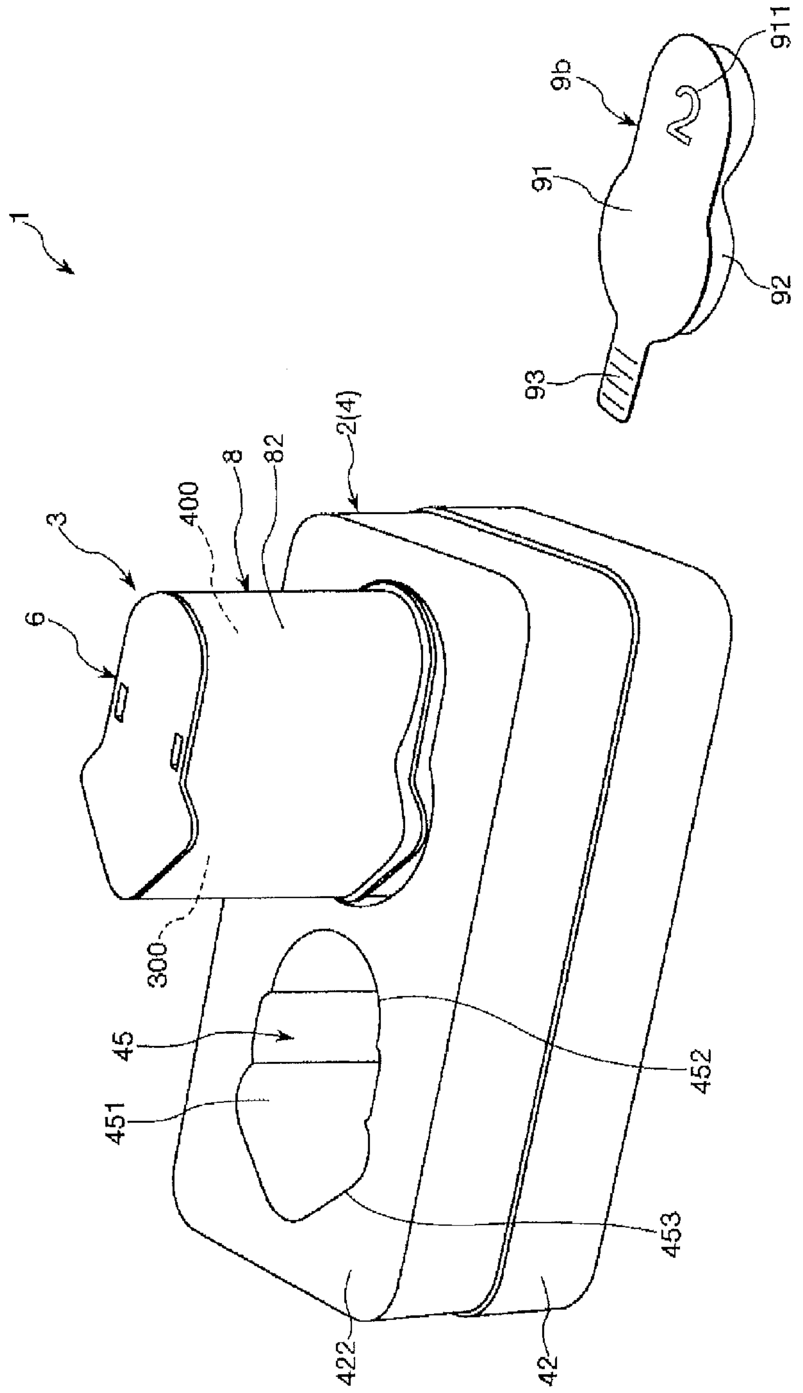
FIG. 14 is a view for describing sequentially the method of using the connector shown in FIG. 1.

In addition, as shown in FIGS. 14 and 15, the medicine-side loading member 5 is connected to the connector for mixing 3 together with the first medicine container 100 and the second medicine container 200. The medicine-side loading member 5 is taken out of the holder main body 4 together with the first medicine container 100 and the second medicine container 200, by pulling the connector for mixing 3 upward in the condition where the medicine-side loading member 5 is connected to the connector for mixing 3. For this purpose, the engaging force between the engaging portion 511 of the medicine-side loading member 5 and the side wall 42 of the holder main body 4 is set to be smaller than the connecting force between the connector for mixing 3 and the medicine-side loading member 5. This helps ensure that when the connector for mixing 3 is pulled upward in the connected condition in which the medicine-side loading member 5 and the connector for mixing 3 are connected with each other (the condition shown in FIG. 14), the connected condition is inhibited or prevented from being released. Consequently, the first medicine container 100 and the second medicine container 200 can be taken out of the holder main body 4, together with the medicine-side loading member 5.

The manner in which the engaging force between the engaging portion 511 of the medicine-side loading member 5 and the side wall 42 of the holder main body 4 is set to be smaller than the connecting force between the connector for mixing 3 and the medicine-side loading member 5 is not particularly limited. As an example, the engagement area between the engaging portion 511 and the side wall 4 can be made smaller than the connection area connecting the connector for mixing 3 and the medicine-side loading member 5.

The material constituting the medicine-side loading member 5 is not specifically restricted. Examples of materials which can be used to fabricate the medicine-side loading member 5 include the materials mentioned above in relation to the holder main body 4 can be used.

As shown in FIG. 5, in the liquid-side containing section 45 of the holder main body 4, a liquid-side loading member 6 is contained together with the first liquid container 300 and the second liquid container 400. The liquid-side loading member 6 is to be loaded with the first liquid container 300 and the second liquid container 400.

Figure 7:
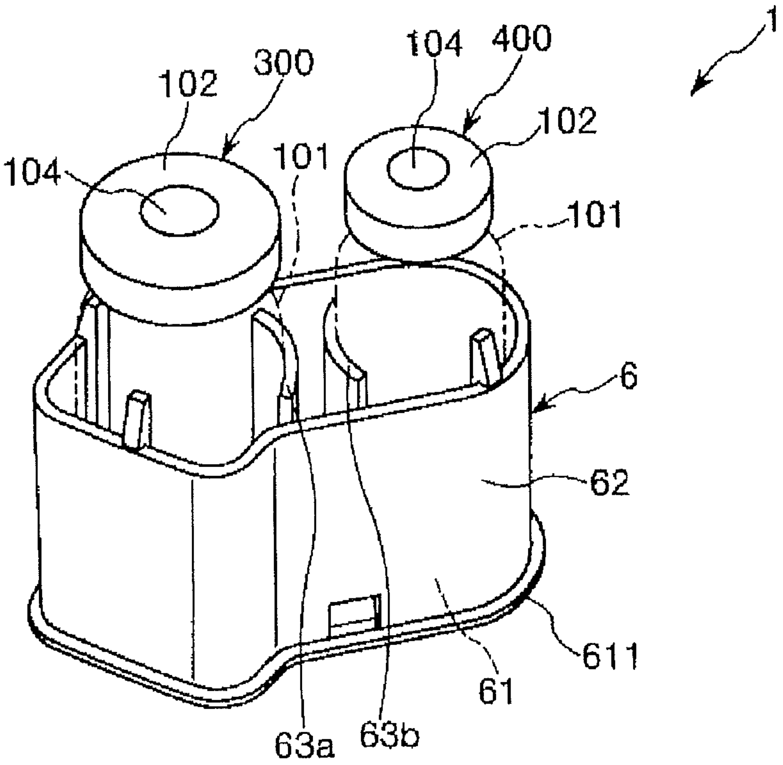
FIG. 7 is a perspective view of the liquid-side loading member of the medical container holder shown in FIG. 4 loaded with a liquid container.

As shown in FIG. 7, the liquid-side loading member 6 has a bottom section 61, an upstanding outer wall 62 extending upwardly from the bottom section 61, and upstanding inner walls 63*a* and 63*b* extending upwardly from the bottom section 61 on the inside of the outer wall 62.

The bottom section 61 is a section possessing a plan-view shape which conforms to the shape (arrow-like shape) of a liquid-side insertion port 451 of the liquid-side containing section 45 of the holder main body 4 which will be described later. In addition, the bottom section 61 supports bottom portions of the medicine containers so that the height of the port section 102 of the first liquid container 300 and the height of the port section 102 of the second liquid container 400 are substantially the same (i.e., the top of the port sections 102 of the two containers 300, 400 is at the same vertical position). This helps ensure that when the stoppers 104 press fitted in the port sections 102 are disinfected by use of an absorbent cotton impregnated with a disinfectant, for example, the stoppers 104 can be disinfected with the absorbed cotton all together, so that the disinfecting operation can be carried out easily.

The outer wall 62 is integrally formed in one piece with the bottom section 61. The outer wall 62 is formed along an edge portion of the bottom section 61. The height of the outer wall 62 is lower than the height of the first liquid container 300 and the second liquid container 400 when the containers 300, 400 are loaded in the liquid-side loading member 6 (see FIGS. 5 and 7).

The inner wall 63*a* cooperates with the outer wall 62 to hold or clamp the first liquid container 300 therebetween. The inner wall 63*a* is plate-shaped and curved in an arched shape to generally correspond to the curvature of the outer-peripheral shape of the bottle main body 101 of the first liquid container 300. The inner wall 63*a* projects upwardly in an integral manner from the bottom section 61.

The inner wall 63*b* cooperates with the outer wall 62 to clamp or hold the second liquid container 400 therebetween. The inner wall 63*a* is plate-shaped and curved in an arched shape to generally correspond to the curvature of the outer-peripheral shape of the bottle main body 101 of the second liquid container 400. The inner wall 63*b* projects upwardly in an integral manner from the bottom section 61.

Figure 13:
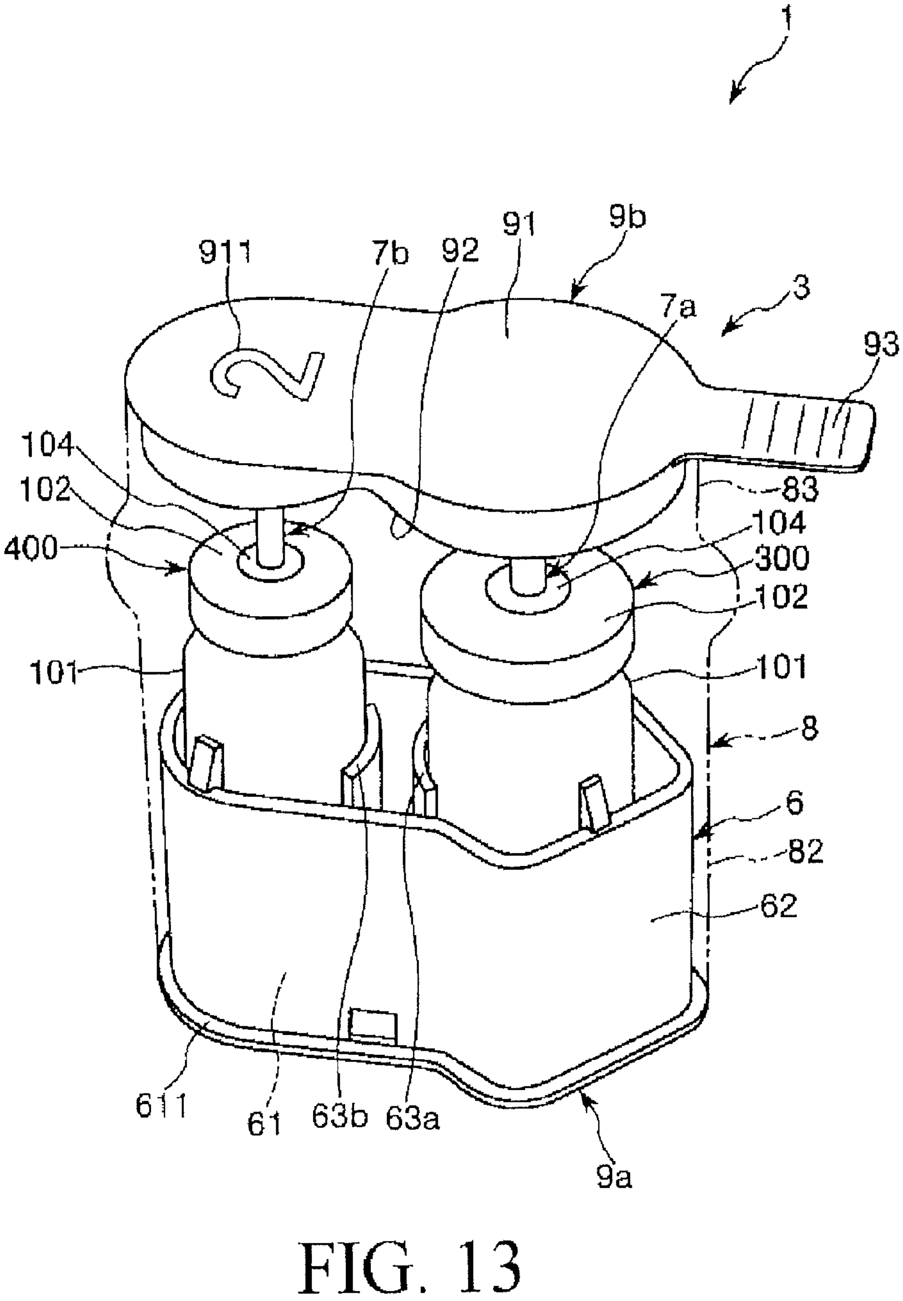
FIG. 13 is a view for describing sequentially the method of using the connector shown in FIG. 1.

In the liquid-side loading member 6 thus configured, the first liquid container 300 and the second liquid container 400 can be held all together. In addition, as shown in FIG. 13, the first liquid container 300 and the second liquid container 400 held in the liquid-side loading member 6 can be taken out of (removed from) the holder main body 4, together with the liquid-side loading member 6. This helps ensure that even when the first liquid container 300 and the second liquid container 400 are taken out of the holder main body 4, the positional relationship between these liquid containers 300, 400 is maintained. Consequently, the first medicine container 100 can be relatively assuredly connected to the appropriate one of the containers 300, 400 (i.e., the first medicine container 100 can be relatively assuredly connected to the first liquid container 300), and the second medicine container 200 can be relatively assuredly connected to the appropriate one of the containers 300, 400 (i.e., the second medicine container 100 can be relatively assuredly connected to the second liquid container 400), and intermediated by the connector for mixing 3.

In addition, as shown in FIGS. 5 and 7, the bottom section 61 has an edge portion protruding to the outside beyond the outer wall 62. As shown in FIG. 5, this edge portion functions as an engaging portion 611 for engagement with a lower portion of the inner surface 421 of the side wall 42 defining the liquid-side containing section 45 of the holder main body 4. The engagement of the engaging portion 611 of the liquid-side loading member 6 with the side wall 42 of the holder main body 4 helps ensure that the liquid-side loading member 6 is relatively assuredly fixed to the holder main body 4. Consequently, even if the holder 2 is inverted upside down, the liquid-side loading member 6 as well as the first liquid container 300 and the second liquid container 400 held in the liquid-side loading member 6, are inhibited or prevented from falling out of the holder main body 4.

Figure 12:
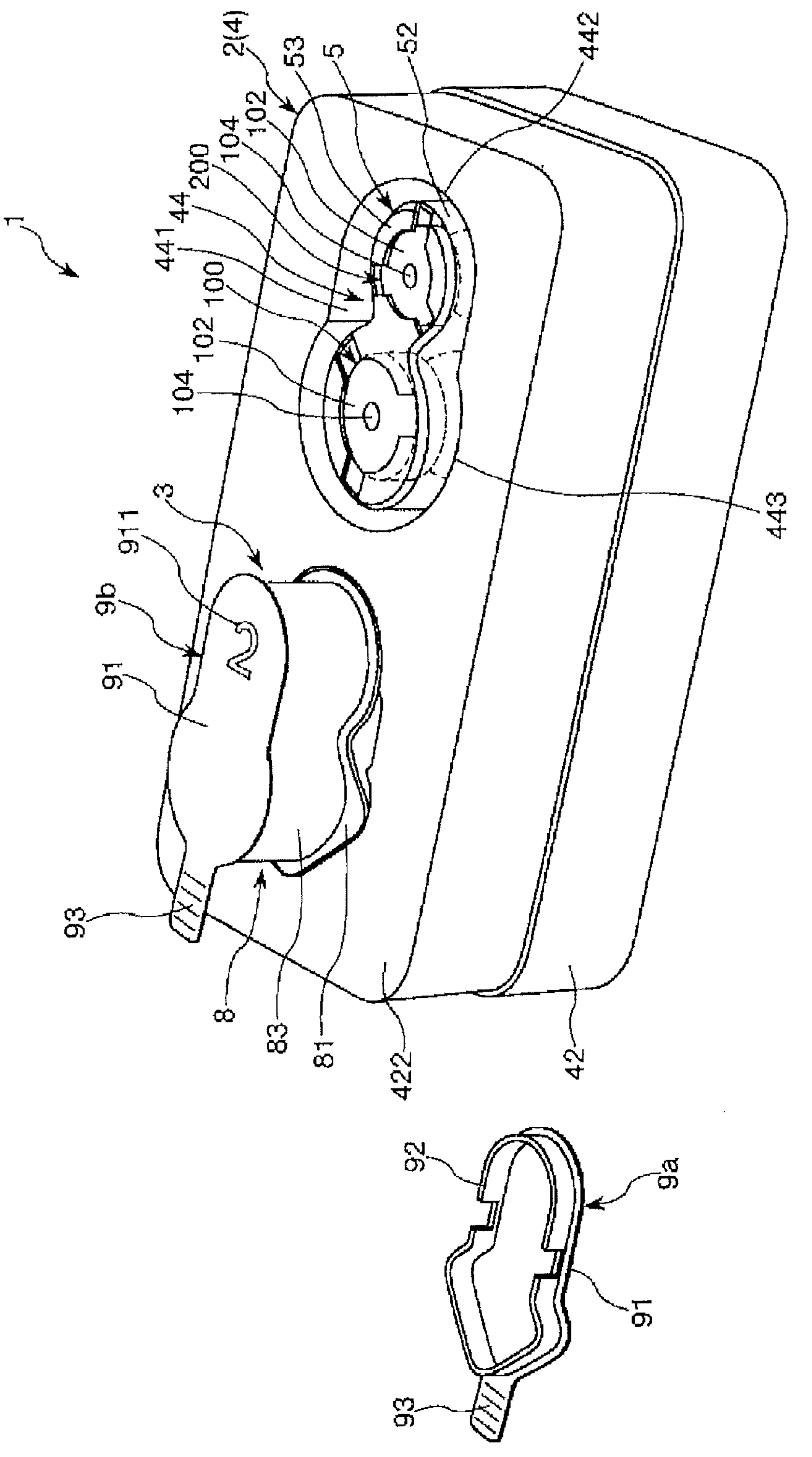
FIG. 12 is a view for describing sequentially a method of using the connector shown in FIG. 1.

As shown in FIGS. 12 and 13, the liquid-side loading member 6 is connected to the connector for mixing 3 together with the first liquid container 300 and the second liquid container 400. The liquid-side loading member 6 is taken out of the holder main body 4 together with the first liquid container 300 and the second liquid container 400, by pulling the connector for mixing 3 upward in the condition where the liquid-side loading member 6 is connected to the connector for mixing 3. For this purpose, the engaging force between the engaging portion 611 of the liquid-side loading member 6 and the side wall 42 of the holder main body 4 is smaller than the connecting force between the connector for mixing 3 and the liquid-side loading member 6. This helps ensure that when the connector for mixing 3 is pulled upward in the connected condition in which the liquid-side loading member 6 and the connector for mixing 3 are connected to each other (the condition shown in FIG. 12), the connected condition is inhibited or prevented from being released. Consequently, the first liquid container 300 and the second liquid container 400 can be taken out of the holder main body 4, together with the liquid-side loading member 6.

The manner in which the engaging force between the engaging portion 611 of the liquid-side loading member 6 and the side wall 42 of the holder main body 4 is smaller than the connecting force between the connector for mixing 3 and the liquid-side loading member 6 is not particularly limited. As an example, the engagement area between the engaging portion 611 and the side wall 4 is smaller than the connection area connecting the connector for mixing 3 and the liquid-side loading member 6.

The material constituting the liquid-side loading member 6 is not specifically restricted. Examples of materials which can be used to fabricate the liquid-side loading member 6 include the materials mentioned above in relation to the holder main body 4.

The connector for mixing 3 is so configured that one-end-side portion can be collectively connected to the first liquid container 300 and the second liquid container 400 (see FIGS. 12 and 13), and other-end-side portion can be collectively connected to the first medicine container 100 and the second medicine container 200 (see FIGS. 14 and 15). In connecting these containers to the connector for mixing 3, the first liquid container 300 and the second liquid container 400 are first connected, and thereafter the first medicine container 100 and the second medicine container 200 are connected. Then, the first liquid container 300 and the first medicine container 100 are interconnected, and the second liquid container 400 and the second medicine container 200 are interconnected, through the connector for mixing 3.

As shown in FIG. 9, the connector for mixing 3 includes: the first double-pointed needle 7*a* and the second double-pointed needle 7*b* which are hollow; a hub 8 linking and supporting the first double-pointed needle 7*a* and the second double-pointed needle 7*b*; and a liquid-side cap 9*a* and a medicine-side cap 9*b* which are detachably attached to the hub 8.

The first double-pointed needle 7*a* and the second double-pointed needle 7*b* are parallel to each other. The configuration of the first double-pointed needle 7*a* and that of the second double-pointed needle 7*b* are the same, and so the following description of the first double-pointed needle 7*a* applies to the second double-pointed needle 7*b*.

The first double-pointed needle 7*a* can be divided into a liquid-side needle 71 which is a sharpened end located on one end side and a medicine-side needle 72 which is a sharpened end located on the other end side and communicates with the liquid-side needle 71. The liquid-side needle 71 can pierce the stopper 104 of the first liquid container 300 when the connector for mixing 3 is connected to the first liquid container 300 (see FIG. 13). The medicine-side needle 72 can pierce the stopper 104 of the first medicine container 100 when the connector for mixing 3 is connected to the first medicine container 100.

The material constituting the first double-pointed needle 7*a* is not particularly limited. Examples of materials which can be used include various metallic materials and rigid resin materials as mentioned above in relation to the holder main body 4.

With respect to the second double-pointed needle 7*b*, a liquid-side needle 71 can pierce the stopper 104 of the second liquid container 400 when the connector for mixing 3 is connected to the second liquid container 400 (see FIG. 13). In addition, a medicine-side needle 72 of the second double-pointed needle 7*b* can pierce the stopper 104 of the second medicine container 200 when the connector for mixing 3 is connected to the second medicine container 200.

The first double-pointed needle 7*a* and the second double-pointed needle 7*b* are preferably equal (inclusive of substantially equal) in thickness (diameter) and length in the configuration shown in FIG. 9. But the first and second double-pointed needles 7*a*, 7*b* are not limited in this regard as the double-pointed needles 7*a*, 7*b* may possess different thicknesses (diameters) and/or lengths.

The hub 8 is disposed on the outer periphery side of the first double-pointed needle 7*a* and the second double-pointed needle 7*b*. The hub 8 is generally tube-shaped, and is provided at its intermediate portion with a support section 81 supporting intermediate portions of the first double-pointed needle 7*a* and the second double-pointed needle 7*b*. The portion of the hub 8 on the side of the liquid-side needles 71 (the lower side in FIG. 9) relative to the support section 81 is a liquid-side tube-shaped section 82 which covers the respective liquid-side needles 71 of the first double-pointed needle 7*a* and the second double-pointed needle 7*b* up to their needle points. As shown in FIG. 13, the liquid-side tube-shaped section 82 is configured to be fitted onto the outer wall 62 of the liquid-side loading member 6.

In addition, the portion of the hub 8 which is on the side of the medicine-side needles 72 (the upper side in FIG. 9) relative to the support section 81 is a medicine-side tube-shaped section 83 which covers the respective medicine-side needles 72 of the first double-pointed needle 7*a* and the second double-pointed needle 7*b* up to their needle points. As shown in FIG. 15, the medicine-side tube-shaped section 83 is configured to be fitted onto the wall section 52 of the medicine-side loading member 5.

Figure 10:
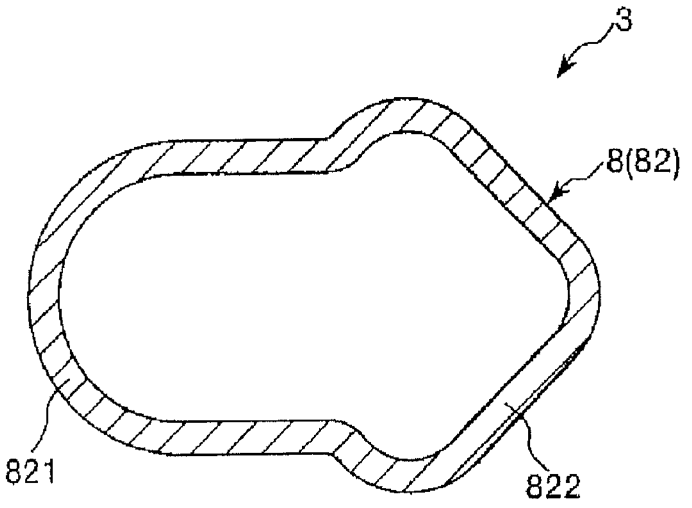
FIG. 10 is a cross-sectional view of the connector taken along the section line X-X of FIG. 9.
Figure 11:
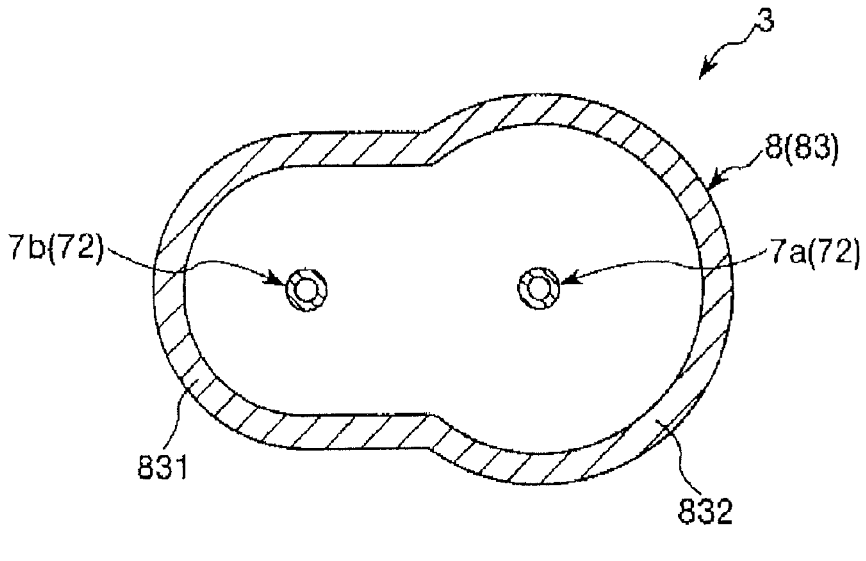
FIG. 11 is a cross-sectional view of the connector taken along the section line XI-XI in FIG. 9.

As shown in FIGS. 10 and 11, the contour shape in cross-section (the outer peripheral shape) of the liquid-side tube-shaped section 82 and that of the medicine-side tube-shaped section 83 are different from each other. Specifically, the contour shape in cross-section of the liquid-side tube-shaped section 82 is an arrow-shape, whereas the contour shape in cross-section of the medicine-side tube-shaped section 83 is a daruma-shape or gourd-shape. This will be described in more detail later.

As shown in FIG. 12, when the connector for mixing 3 is connected to the first liquid container 300 and the second liquid container 400, the medicine-side tube-shaped section 83 protrudes to the upper side beyond an upper portion 422 of the side wall 42 of the holder main body 4. This helps ensure that the connector for mixing 3 can be rather assuredly gripped at the time of taking out the first liquid container 300 and the second liquid container 400 from the holder main body 4, so that the taking-out or removing operation can be carried out relatively easily and securely. Then, transition to a connecting operation for connecting the connector for mixing 3 to the first medicine container 100 and the second medicine container 200 can be made rather swiftly.

As shown in FIG. 14, when the connector for mixing 3 is connected to the first medicine container 100 and the second medicine container 200, the liquid-side tube-like section 82 protrudes to the upper side beyond the upper portion 422 of the side wall 42 of the holder main body 4. This helps ensure that the connector for mixing 3 can be fairly assuredly gripped at the time of taking out the first medicine container 100 and the second medicine container 200 from the holder main body 4, so that the taking-out or removing operation can be performed relatively easily and securely. Then, after the taking-out, transition to a detaching operation for detaching the connector for mixing 3 from the first medicine container 100 and the second medicine container 200 and transition to a connecting operation for connecting the first syringe 600 and the second syringe 700 respectively to the first medicine container 100 and the second medicine container 200 detached from the connector for mixing 3 can be performed rather rapidly.

The material constituting the hub 8 is not specifically limited. Examples of materials which can be used to fabricate the hub 8 include the various metallic materials and rigid resin materials as mentioned above in the description of the holder main body 4.

As shown in FIG. 9, the liquid-side cap 9*a* is detachably attached to the liquid-side tube-shaped section 82 of the hub 8, whereas the medicine-side cap 9*b* is detachably attached to the medicine-side tube-shaped section 83. The liquid-side cap 9*a* and the medicine-side cap 9*b* possess the same configuration, except for shape. Thus, the following description of the liquid-side cap 9*a* applies also to the medicine-side cap 9*b*.

The liquid-side cap 9*a* includes a base 91 having a long plate-shaped shape, a rib 92 projecting from a surface of the base 91 on one side (the upper side in FIG. 9) of the base 91, and a tab 93 projecting from an edge portion of the base 91.

In the liquid-side cap 9*a*, the base 91 has a plan-view shape which is the same (inclusive of substantially the same) as the contour shape in cross-section of the liquid-side tube-shaped section 82.

The rib 92 is integrally formed in one piece with the base 91, along an edge portion of the base 91.

The tab 93 is composed of a tongue piece formed as one body with the base 91, on one end side of the base.

Of the liquid-side cap 9*a* thus configured, the rib 92 is fitted in the liquid-side tube-shaped section 82 of the hub 8. This helps ensure that the liquid-side cap 9*a* is mounted to the liquid-side tube-shaped section 82, and, in the mounted state, it can cover the liquid-side needle 71 of the first double-pointed needle 7*a* and the second double-pointed needle 7*b*, together with the liquid-side tube-shaped section 82. In addition, at the time of taking off the liquid-side cap 9*a* in the mounted state from the liquid-side tube-shaped section 82, the taking-off operation can be carried out by gripping the tab 93 (see FIG. 12).

With respect to the medicine-side cap 9*b*, the rib 92 is fitted to the medicine-side tube-shaped section 83 of the hub 8. This helps ensure that the medicine-side cap 9*b* is mounted to the medicine-side tube-shaped section 83, and, in the mounted state, it can cover the medicine-side needle 72 of the first double-pointed needle 7*a* and the second double-pointed needle 7*b*, together with the medicine-side tube-like section 83. In addition, at the time of taking off or removing the medicine-side cap 9*b* in the mounted state from the medicine-side tube-shaped section 83, the taking-off operation can be performed by gripping the tab 93 (see FIG. 14).

As has been described above, the connector for mixing 3 is so configured that, at the time of connecting the connector for mixing 3 to the first medicine container 100, the second medicine container 200, the first liquid container 300 and the second liquid container 400, the first liquid container 300 and the second liquid container 400 are connected prior to the first medicine container 100 and the second medicine container 200 (see FIGS. 12 to 15).

The liquid-side cap 9*a* and the medicine-side cap 9*b* of the connector for mixing 3 are provided with corresponding marks 911 indicative of the order in which to connect the containers. As the mark 911, the base 91 of the liquid-side cap 9*a* is provided with numeral "1" (not shown), and the base 91 of the medicine-side cap 9*b* is provided with numeral "2."

With such marks 911 thus provided, the connecting operations at the time of connecting the connector for mixing 3 to the containers can be carried out properly.

Specifically, first, the liquid-side cap 9*a* provided with numeral "1" is dismounted or removed, and the first liquid container 300 and the second liquid container 400 are connected to the liquid-side tube-like section 82 from which the liquid-side cap 9*a* has been dismounted. Next, the medicine-side cap 9*b* provided with numeral "2" is dismounted or removed, and the first medicine container 100 and the second medicine container 200 are connected to the medicine-side tube-like section 83 from which the medicine-side cap 9*b* has been dismounted.

The material or materials constituting the liquid-side cap 9*a* and the medicine-side cap 9*b* are not particularly limited. For example, various rigid resin materials as mentioned above in the description of the holder main body 4 can be used.

As has been described above, in the medical instrument set 1, the connector for mixing 3 is connected to the first liquid container 300 and the second liquid container 400, prior to connecting it to the first medicine container 100 and the second medicine container 200.

At the time of connecting the connector for mixing 3 to the first liquid container 300 and the second liquid container 400, the connecting operation is conducted in the condition where the first liquid container 300 and the second liquid container 400 have their port sections 102 oriented upward (see FIG. 12). If the connecting operation is performed in the condition where the first liquid container 300 and the second liquid container 400 have their port sections 102 oriented downward, the liquid inside the first liquid container 300 would flow out through the first double-pointed needle 7*a* piercing the stopper 104 of the first liquid container 300, and the liquid inside the second liquid container 400 would flow out through the second double-pointed needle 7*b* piercing the stopper 104 of the second liquid container 400.

In addition, at the time of connecting the connector for mixing 3 with the first liquid container 300 and the second liquid connector 400 connected thereto, to the first medicine container 100 and the second medicine container 200, the connecting operation is carried out in the condition where the first medicine container 100 and the second medicine container 200 have their port sections 102 oriented upward (see FIG. 14). If the connecting operation is conducted in the condition where the first medicine container 100 and the second medicine container 200 have their port sections 102 oriented downward, the negative pressure condition kept inside the first liquid container 300 would result in the liquid not being transferred from the inside of the first liquid container 300, and only air inside the first liquid container 300 would be transferred into the first medicine container 100, so that the medicine inside the first medicine container 100 would not be diluted with the liquid sufficiently. Similarly, since the inside of the second liquid container 400 is also in a negative pressure condition, the liquid would not be transferred from the inside the second liquid container 400, and only air inside the second liquid container 400 would be transferred into the second medicine container 200, so that the medicine inside the second medicine container 200 cannot be dissolved by the liquid sufficiently.

Thus, in the medical instrument set 1, at the times of performing the liquid container connecting operation of connecting the connector for mixing 3 to the first liquid container 300 and the second liquid container 400, and the medicine container connecting operation of connecting the connector for mixing 3 to the first medicine container 100 and the second medicine container 200, both the operations are carried out in the condition where the containers are in upright states.

The holder 2 is so configured that such connecting operations are performed rather assuredly. This will be described below.

As shown in FIG. 5, the holder main body 4 is so designed that the height of the side wall 42 is higher than the heights of the first liquid container 300 and the second liquid container 400 while the containers 300, 400 are held in the held state by the holder main body 4. This helps ensure that the first liquid container 300 and the second liquid container 400 in the held state can be prevented from being taken out of the holder main body 4 by directly gripping the containers. This makes it possible to mount the holder main body 4 (holder 2) onto the above-mentioned support base and to apply the liquid container connecting operation to the first liquid container 300 and the second liquid container 400, which are held on the holder main body 4 in the upright state, appropriately and rather assuredly (see FIG. 12). While the height of the side wall 42 of the holder main body 4 is higher than the heights of the first liquid container 300 and the second liquid container 400 when the containers 300, 400 are held in the configuration shown in FIG. 5, other configurations are possible. For example, the height of the side wall 42 may be the same as the height of each of the containers 300, 400 when the containers 300, 400 are in the held state.

The first liquid container 300 and the second liquid container 400 can be taken out of the holder main body 4 by lifting the connector for mixing 3 connected to the first liquid container 300 and the second liquid container 400 (the liquid-side loading member 6) by the liquid container connecting operation (see FIG. 13).

As shown in FIG. 6, the height of the side wall 42 of the holder main body 4 is higher than the heights of the first medicine container 100 and the second medicine container 200 when the containers 100, 200 are held in the held state by the holder main body 4. This helps ensure that the first medicine container 100 and the second medicine container 200 in the held state are inhibited or prevented from being taken out of the holder main body 4 by directly gripping the containers. This makes it possible to mount the holder main body 4 (holder 2) onto the support base and to apply the medicine container connecting operation to the first medicine container 100 and the second medicine container 200, which are held on the holder main body 4 in the upright state, appropriately and rather assuredly (see FIG. 14). While the height of the side wall 42 of the holder main body 4 is higher than the heights of the first medicine container 100 and the second medicine container 200 when the containers 100, 200 are held in the configuration shown in FIG. 5, other configurations are possible. For example, the height of the side wall 42 may be the same as the height of each of the containers 100, 200 when the containers 100, 200 are in the held state.

The first medicine container 100 and the second medicine container 200 can be taken out of the holder main body 4 by lifting up the connector for mixing 3 connected to the first medicine container 100 and the second medicine container 200 (the medicine-side loading member 5) by the medicine container connecting operation (see FIG. 15).

Thus, in the holder 2, the side wall 42 of the holder main body 4 functions as a take-out preventive means for preventing each of the containers in the held state from being taken out of the holder main body 4 by gripping the container. This makes it possible to appropriately perform the liquid container connecting operation and the medicine container connecting operation, as above-mentioned.

In addition, as shown in FIGS. 5 and 6, the side wall 42 of the holder main body 4 has its inner surface 421 slanted toward the outside. This helps facilitate the taking-out or removing operation of the containers as above-mentioned.

Furthermore, the medical instrument set 1 is so configured that the first liquid container 300 and the second liquid container 400 are rather assuredly connected to the liquid-side needle 71 side of the connector for mixing 3, and that the first medicine container 100 and the second medicine container 200 are rather assuredly connected to the medicine-side needle 72 side. In other words, this configuration prevents a connection mode in which the first medicine container 100 and the second medicine container 200 are connected to the liquid-side needle 71 side of the connector for mixing 3, and the first liquid container 300 and the second liquid container 400 are connected to the medicine-side needle 72 side (i.e., a connection mode in which the connectors are connected to inappropriate sides of the connector for mixing 3). This is described in more detail below.

As shown in FIGS. 10 and 11, the liquid-side tube-shaped section 82 and the medicine-side tube-shaped section 83 of the hub of the connector for mixing 3 are different from each other in contour shape in cross-section (hereinafter referred to simply as "contour shape").

The contour shape of the liquid-side tube-shaped section 82 is an arrow-shape.

Specifically, the liquid-side tube-shaped section 82 has a circular portion 821 which is circular in cross section and a tetragonal portion 822 of which the cross-sectional shape is a tetragon having a diagonal longer than the diameter of the circular portion 821. The circular portion 821 and the tetragonal portion 822 are in such a state that their centers are deviated from each other in the direction of one of the two diagonals. The contour shape of the liquid-side tube-shaped section 82 is a shape as if obtained by interconnecting the circular portion 821 and the tetragonal portion 822 which are in the deviated state as just-mentioned. One end of the cross-section of the liquid-side tube-shaped section 82 is thus curved (the left end in FIG. 10) and the opposite end of the cross-section of the liquid-side tube-shaped section 82 is pointed or arrow-shaped (the right end in FIG. 10).

On the other hand, the contour shape of the medicine-side tube-shaped section 82 is a daruma-shape or gourd-shape, which is significantly different from, and incompatible with, the contour shape of the liquid-side tube-shaped section 82.

More specifically, the medicine-side tube-shaped section 83 has a smaller circular portion 831 and a larger circular portion 832 which are circular in cross-section. The smaller circular portion 831 possesses a diameter of which is smaller than the diameter of the large circular portion 832. The smaller circular portion 831 and the larger circular portion 832 are in such a state that their centers are deviated from each other in a radial direction. The overall contour shape of the medicine-side tube-shaped section 83 is a shape obtained by interconnecting the small circular portion 831 and the large circular section 832 which are in the deviated state as just-mentioned. Both ends of the cross-section of the liquid-side tube-shaped section 83 are thus curved.

In this embodiment, the contour shape of the liquid-side tube-shaped section 82 is the arrow-shape, whereas the contour shape of the medicine-side tube-shaped section 83 is the daruma-shape or gourd-shape. This configuration, however, is not limitative. For example, a configuration may be adopted in which the contour shape of the liquid-side tube-shaped section 82 is a daruma-shape or gourd-shape, whereas the contour shape of the medicine-side tube-shaped section 83 is an arrow-shape.

As shown in FIG. 4, in the holder 2, the aperture of the liquid-side containing section 4, or the liquid-side insertion port 451, has a shape conforming to the contour shape of the liquid-side tube-shaped section 82.

In other words, the liquid-side insertion port 451 has a circular portion 452 which is slightly greater in size than the circular portion 821 of the liquid-side tube-shaped section 82, and a tetragonal portion 453 which is slightly greater in size than the tetragonal portion 822. The circular portion 452 and the tetragonal portion 453 liquid-side insertion port 451 are deviated (spaced apart) from one another, like the circular portion 821 and the tetragonal portion 822 of the liquid-side tube-shaped section 82.

Such a shape of the liquid-side insertion port 451 continues to the bottom plate 41 of the liquid-side containing section 45.

In addition, the aperture of the medicine-side containing section 44 of the holder main body 4, or the medicine-side insertion port 441, has a shape conforming to the contour shape of the medicine-side tube-shaped section 83.

In other words, the medicine-side insertion port 441 has a smaller circular portion 442 which is slightly greater in size than the small circular portion 831 of the medicine-side tube-shaped section 83, and a larger circular portion 443 which is slightly greater in size than the large circular portion 832. The smaller circular portion 442 and the larger circular portion 443 of the medicine-side insertion port 441 are deviated (spaced apart0 from one another, like the smaller circular portion 831 and the larger circular portion 832 of the medicine-side tube-shaped section 83.

Such a shape of the medicine-side insertion port 441 continues to the bottom plate 41 of the medicine-side containing section 44.

In the medical instrument set 1 shaped as above-described, the connector for mixing 3 is first connected to the first liquid container 300 and the second liquid container 400. In this instance, the liquid container connecting operation is conducted in the condition where the liquid-side needle 71 side of the connector for mixing 3 is oriented toward the first liquid container 300 and the second liquid container 400. In this case, the contour shape of the liquid-side tube-like section 82 present on the liquid-side needle 71 side of the connector for mixing 3 conforms to the shape of the liquid-side insertion port 451 of the liquid-side containing section 45 in which is held the first liquid container 300 and the second liquid container 400. Therefore, the liquid-side tube-like section 82 can pass through the liquid-side insertion port 451. This helps ensure that the liquid-side needle 71 of the first double-pointed needle 7*a* of the connector for mixing 3 pierces the stopper 104 of the first liquid container 300, and the liquid-side needle 71 of the second double-pointed needle 7*b* pierces the stopper 104 of the second liquid container 400. Associated with these piercing operations, the liquid-side tube-shaped section 82 of the hub 8 of the connector for mixing 3 is fitted onto the outer wall 62 of the liquid-side loading member 6.

On the other hand, in the case where the liquid-side needle 71 side of the connector for mixing 3 is oriented toward the first medicine container 100 and the second medicine container 200 at the time of performing the liquid container connecting operation, there exists a difference between the contour shape of the liquid-side tube-shaped section 82 of the connector for mixing 3 and the shape of the medicine-side insertion port 441 of the medicine-side containing section 44 containing the first medicine container 100 and the second medicine container 200, and so the liquid-side tube-like section 82 cannot pass through the medicine-side insertion port 441. This helps ensure that a misconnection can be securely inhibited or prevented from occurring at the time of performing the liquid container connecting operation and, hence, the connecting operation can be carried out properly.

In the case where the medicine-side needle 72 side of the connector for mixing 3 is oriented toward the first liquid container 300 and the second liquid container 400 at the time of performing the liquid container connecting operation, there exists a difference between the counter shape of the medicine-side tube-shaped section 83 present on the medicine-side needle 72 side of the connector for mixing 3 and the shape of the liquid-side insertion port 451 of the liquid-side containing section 45. Therefore, the medicine-side tube-shaped section 83 cannot pass through the liquid-side insertion port 451. This helps ensure that a misconnection can be securely prevented from occurring at the time of performing the liquid container connecting operation and, hence, the connecting operation can be conducted properly.

After the liquid container connecting operation is carried out properly, the connector for mixing 3 with the first medicine container 100 and the second medicine container 200 connected is drawn up and inverted upside down, and the connector for mixing 3 is connected to the first medicine container 100 and the second medicine container 200. In this instance, the medicine container connecting operation is conducted in the condition where the medicine-side needle 72 side of the connector for mixing 3 is directed toward the first medicine container 100 and the second medicine container 200. In this case, the contour shape of the medicine-side tube-shaped section 83 present on the medicine-side needle 72 side of the connector for mixing 3 conforms to the shape of the medicine-side insertion port 441 of the medicine-side containing section 44 in which is contained the first medicine container 100 and the second medicine container 200. Therefore, the medicine-side tube-like section 83 can pass through the medicine-side containing section 44. This helps ensure that the medicine-side needle 72 of the first double-pointed needle 7*a* of the connector for mixing 3 pierces the stopper 104 of the first medicine container 100, and the medicine-side needle 72 of the second double-pointed needle 7*b* pierces the stopper 104 of the second medicine container 200. Associated with these piercing operations, the medicine-side tube-shaped section 83 of the hub 8 of the connector for mixing 3 is fitted onto the wall section 52 of the medicine-side loading member 5.

Thus, in the medical instrument set 1, the liquid container connecting operation and the medicine container connecting operation can be performed in order and properly. In addition, these connecting operations are carried out more assuredly by checking the marks 911 imparted to the liquid-side cap 9*a* and the medicine-side cap 9*b* of the connector for mixing 3.

As shown in FIG. 5, the height of the side wall 42 of the holder main body 4 is higher than the heights of the first liquid container 300 and the second liquid container 400 when the containers 300, 400 are contained in the liquid-side containing section 45 (the holder main body 4). Therefore, the height of the liquid-side insertion port 451 of the liquid-side containing section 45 also is naturally higher than the height of each of the containers. This helps ensure that the first liquid container 300 and the second liquid container 400 in the held state can be inhibited or prevented from being taken out of the holder main body 4 by directly gripping the containers.

In addition, as shown in FIG. 6, the height of the medicine-side insertion port 441 of the medicine-side containing section 44 is higher than the heights of the first medicine container 100 and the second medicine container 200 when the containers 100, 200 are contained in the medicine-side containing section 44. This helps ensure that the first medicine container 100 and the second medicine container 200 in the held state can be prevented from being taken out of the holder main body 4 by directly gripping the containers.

The medical instrument set 1 is so configured that the first liquid container 300 and the first medicine container 100 are interconnected rather assuredly, and the second liquid container 400 and the second medicine container 200 are interconnected rather assuredly, through the connector for mixing 3 (see FIG. 15). In other words, a situation in which the first liquid container 300 and the second medicine container 200 are connected to each other while the second liquid container 400 and the first medicine container 100 are connected to each other is securely inhibited or prevented from occurring. Now, this will be described below.

At the time of performing the liquid container connecting operation, as shown in FIG. 12, the circular portion 821 of the liquid-side tube-shaped section 82 of the connector for mixing 3 and the circular portion 452 of the liquid-side containing section 45 of the holder main body 4 are aligned with each other, whereas the tetragonal portion 822 of the liquid-side tube-like section 82 and the tetragonal portion 453 of the liquid-side containing section 45 are aligned with each other. This helps ensure that the liquid-side tube-like section 82 of the connector for mixing 3 can pass through the liquid-side containing section 45 of the holder main body 4. As a result, the liquid-side needle 71 of the first double-pointed needle 7*a* of the connector for mixing 3 pierces the stopper 104 of the first liquid container 300, whereas the liquid-side needle 71 of the second double-pointed needle 7*b* pierces the stopper 104 of the second liquid container 400. Accordingly, an appropriate liquid container connecting operation is performed.

On the other hand, in the case where the circular portion 821 of the liquid-side tube-shaped section 82 of the connector for mixing 3 and the tetragonal portion 453 of the liquid-side containing section 45 of the holder main body 4 are made to correspond to each other whereas the tetragonal portion 822 of the liquid-side tube-shaped section 82 and the circular portion 452 of the liquid-side containing section 45 are made to correspond to each other, at the time of performing the liquid container connecting operation, the liquid-side tube-shaped section 82 of the connector for mixing 3 cannot pass through the liquid-side containing section 45 of the holder main body 4. In this case, the first liquid container 300 and the second liquid container 400 are not connected to the connector for mixing 3. Specifically, the stopper 104 of the first liquid container 300 is prevented from being pierced by the second double-pointed needle 7*b* which is the improper one of the first double-pointed needle 7*a* and the second double-pointed needle 7*b*, and the stopper 104 of the second liquid container 400 is prevented from being pierced by the first double-pointed needle 7*a* which is the improper one.

After the liquid container connecting operation is conducted properly, the connector for mixing 3 with the first medicine container 100 and the second medicine container 200 connected thereto is drawn up or pulled up, and the medicine container connecting operation is performed. In this instance, as shown in FIG. 14, the smaller circular portion 831 of the medicine-side tube-shaped section 83 of the connector for mixing 3 and the smaller circular portion 442 of the medicine-side containing section 44 of the holder main body 4 are aligned with each other, whereas the larger circular portion 832 of the medicine-side tube-shaped section 83 and the larger circular portion 443 of the medicine-side containing section 44 are aligned with each other. This helps ensure that the medicine-side tube-shaped section 83 of the connector for mixing 3 can pass through the medicine-side containing section 44 of the holder main body 4. As a result, the medicine-side needle 72 of the first double-pointed needle 7*a* of the connector for mixing 3 pierces the stopper 104 of the first medicine container 100, whereas the medicine-side needle 72 of the second double-pointed needle 7*b* pierces the stopper 104 of the second medicine container 200. Consequently, a proper medicine container connecting operation is performed. Accordingly, the first liquid container 300 and the first medicine container 100 are interconnected rather assuredly, and the second liquid container 400 and the second medicine container 200 are interconnected rather assuredly, through the connector for mixing 3.

On the other hand, in the case where the smaller circular portion 831 of the medicine-side tube-shaped section 83 of the connector for mixing 3 and the larger circular portion 443 of the medicine-side containing section 44 of the holder main body 4 are positioned to correspond to each other whereas the large circular portion 832 of the medicine-side tube-shaped section 83 and the smaller circular portion 442 of the medicine-side containing section 44 are positioned to correspond to each other, at the time of performing the medicine container connecting operation, the medicine-side tube-like section 83 of the connector for mixing 3 cannot pass through the medicine-side containing section 44 of the holder main body 4. In this case, the first medicine container 100 and the second medicine container 200 are not connected to the connector for mixing 3. Specifically, the stopper 104 of the first medicine container 100 is inhibited or prevented from being pierced by the second double-pointed needle 7*b* which is the improper one of the first double-pointed needle 7*a* and the second double-pointed needle 7*b*, and the stopper 104 of the second medicine container 200 is inhibited or prevented from being pierced by the first double-pointed needle 7*a* which is the improper one.

Now, the syringe assembly 500 will be described. The syringe assembly 500 includes a first syringe 600, a second syringe 700, and a holder or coupler 800 for holding each of the first and second syringes 600, 700 and for coupling the first syringe 600 and the second syringe 700.

Since the first syringe 600 and the second syringe 700 are substantially the same in configuration except for size, the first syringe 600 will be described below and it is to be understood that this description applies equally to the second syringe 700.

Figure 17:
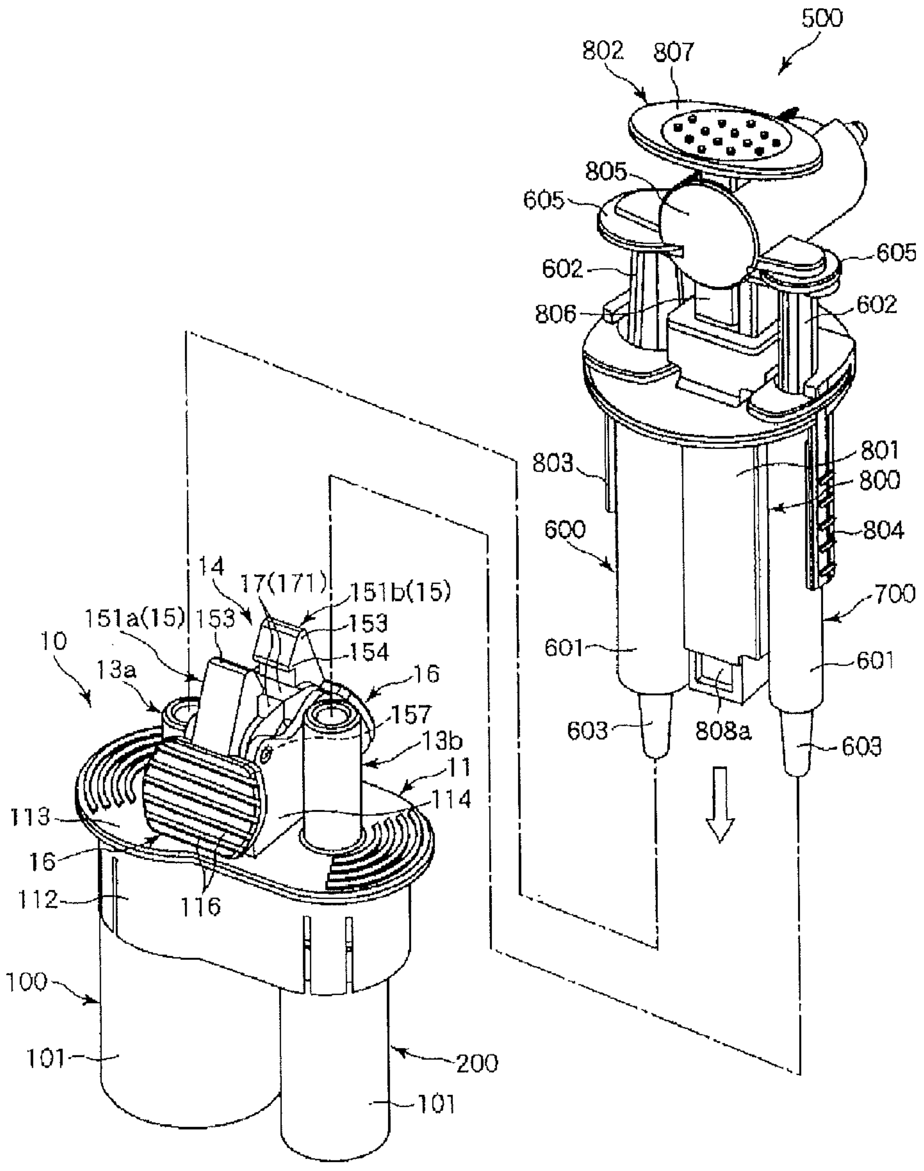
FIG. 17 is a view for describing sequentially the method of using the connector shown in FIG. 1.

As shown in FIGS. 17 to 19, the first syringe 600 includes an outer cylinder (syringe outer cylinder) 601, a gasket positioned inside the syringe outer cylinder 601 and slidable inside the outer cylinder 601, and a plunger 602 for operating the gasket to move along the longitudinal direction (axial direction) of the outer cylinder 601. The gasket is connected and fixed to the leading end of the plunger 602.

The outer cylinder 601 is composed of a bottomed tube-shaped member, and a tube-shaped port 603 reduced in diameter in relation to a barrel portion of the outer cylinder 601 projects integrally from a central portion of a bottom section on the leading end side. In other words, a leading end section of the outer cylinder 601 is the port 603. In addition, an outer peripheral portion of the port 603 has a tapered shape in which the outside diameter gradually decreases toward the leading end (see, for example, FIG. 2).

The outer cylinder 601 is integrally provided, at the outer periphery of the base end thereof, with a flange 605 enlarged in outside diameter.

An outer peripheral surface of the outer cylinder 601 is preferably provided with graduations for indication of the amount of liquid.

The material constituting the outer cylinder 601 is not specifically limited. Examples of materials which can be used to fabricate the outer cylinder 601 include those described above for the bottle main body 101 described above can be used. The outer cylinder 601 is preferably light-transmitting (substantially transparent or semi-transparent), for securing visibility inside the outer cylinder 601.

In such an outer cylinder 601 is contained the gasket formed from an elastic material (e.g., any of the above-mentioned various thermoplastic elastomers).

The plunger 602 is a rod-like member, which is provided on the base end side thereof with a circular disk-like flange 605. The material constituting the plunger 602 can be one of the materials described above for the outer cylinder 601.

Figure 2:
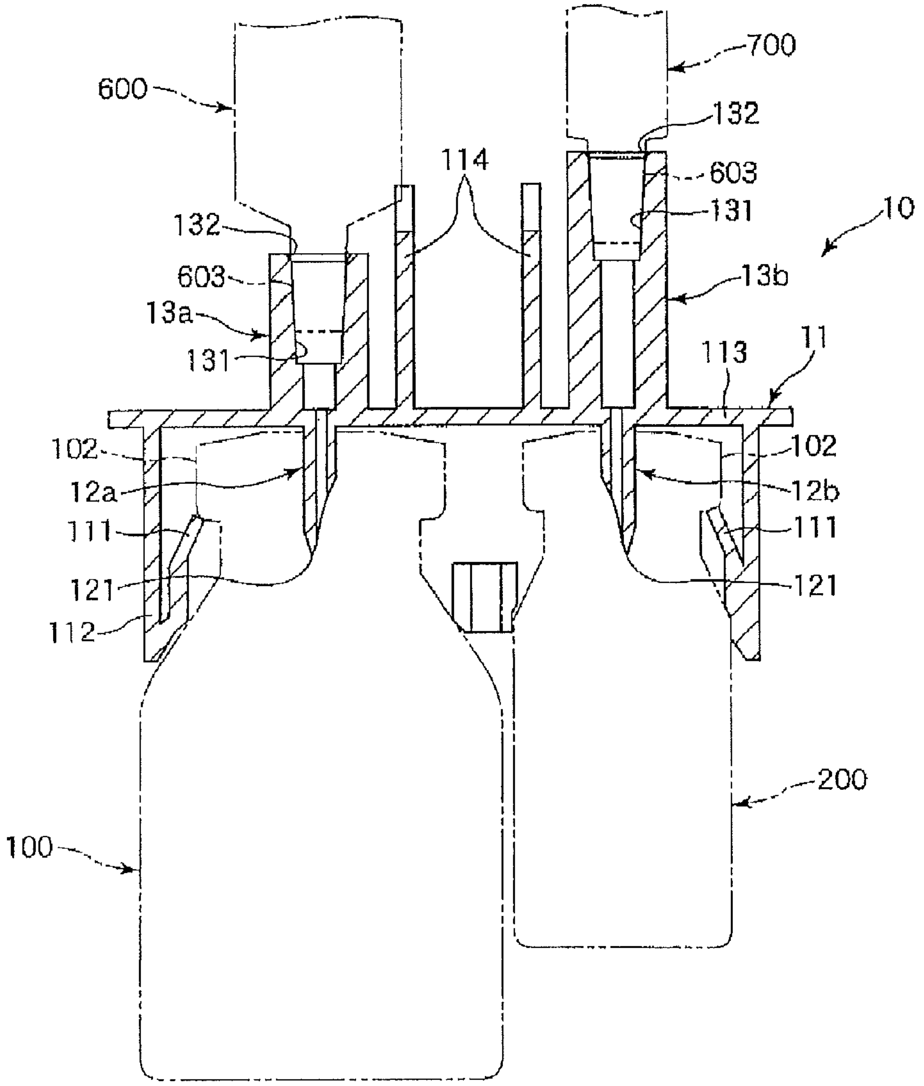
FIG. 2 is a cross-sectional view taken along the section line II-II in FIG. 1.

As shown in FIG. 2, the first syringe 600 is connected to the first medicine container 100 through a connector 10. Then, with the plunger 602 drawn upward under this condition, the medical solution in the first medicine container 100 is sucked and loaded into a space surrounded by the outer cylinder 601 and the gasket.

In addition, like the first syringe 600, the second syringe 700 is also composed of an outer cylinder 601, a gasket slidably positioned in the outer cylinder 601, and a plunger 602 for operating the gasket to move. As shown in FIG. 2, the second syringe 700 is connected to the second medicine container 200 through the connector 10. Then, with the plunger 602 drawn upward under this condition, the medical solution in the second medicine container 200 is sucked and loaded into a space surrounded by the outer cylinder 601 and the gasket.

The coupler 800 is for holding the first syringe 600 and the second syringe 700 in a juxtaposed-in-parallel relationship.

The coupler 800 includes a main body section 801 for collectively holding the first syringe 600 and the second syringe 700, and an operating section 802 for collectively operating the plungers 602 of the first syringe 600 and the second syringe 700.

The main body section 801 is an elongated member, and is provided on opposite sides with a first holding portion 803 for holding the first syringe 600, and a second holding portion 804 for holding the second syringe 700. The first holding portion 803 and the second holding portion 804 are provided with grooves for fitting to outer peripheral portions at intermediate positions in the longitudinal direction of the outer cylinders 601 of the first syringe 600 and the second syringe 700, respectively.

The leading end section of the main body section 801 of the syringe assembly is provided with engagement portions for engagement with portions of the connector 10. In the illustrated embodiment, the engagement portions of the syringe assembly are in the form of two recesses 808*a* and 808*b*, and the portions of the connector 10 which engage the recesses are arms or claws 154 of clamp pieces 151*a* and 152*b* of a fixing means 14 which will be described later (see, for example, FIG. 20). The recesses 808*a* and 808*b* are disposed on opposite sides of a center axis of the main body section 801. In addition, the layout direction of the recesses 808*a* and 808*b* and the layout direction of the first holding portion 803 and the second holding portion 804 are orthogonal to each other.

The operating section 802 applies a pulling operation and a pushing operation to each of the plungers 602 of the first syringe 600 and the second syringe 700. The operating section 802 includes a coupling portion 805 which couples together the flanges 605 of the plungers 602 of the first syringe 600 and the second syringe 700, and an insertion portion 806 which is inserted into the main body section 801.

The coupling portion 805 is a portion by which the flanges 605 of the plungers 602 are coupled together at the same position in the longitudinal direction. This helps ensure that the plungers 602 of the first syringe 600 and the second syringe 700 are operated together at the same time. In addition, at a rear end portion of the coupling portion 805, there is disposed a plate-shaped finger hold section 807 on which a finger can be put at the time of pushing the operating section 802.

The insertion portion 806 is a portion which is guided by the main body section 801 when the operating section 802 is moved along the longitudinal direction. With the insertion portion 806 guided by the main body section 801, the pulling operation and the pushing operation on the operating section 802 can be carried out quite smoothly.

The material constituting the main body section 801 and the operating section 802 is not particularly limited. Examples of materials which can be used to fabricate the main body section 801 and the operating section 802 are the same or similar to those for the bottle main body 101 described above.

The connector 10 disclosed here is to be used with the medicine containers and syringes connected thereto in a process in which a medical solution prepared by mixing a medicine with a liquid is loaded from the first medicine container 100 in which it is contained into the first syringe 600, and a medical solution prepared by mixing a medicine with a liquid is loaded from the second medicine container 200 in which it is contained into the second syringe 700 (see FIGS. 16 to 19).

Figure 1:
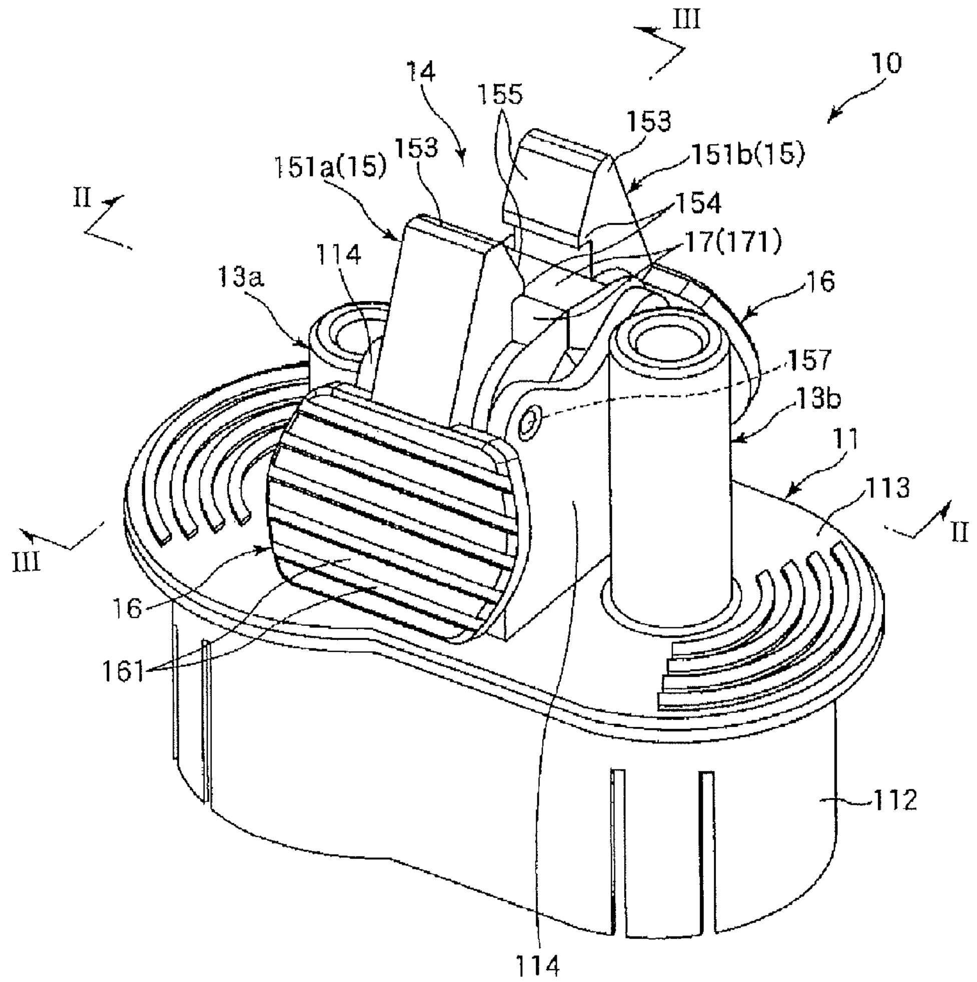
FIG. 1 is a perspective view showing a connector (connector for loading) disclosed here.
Figure 3:
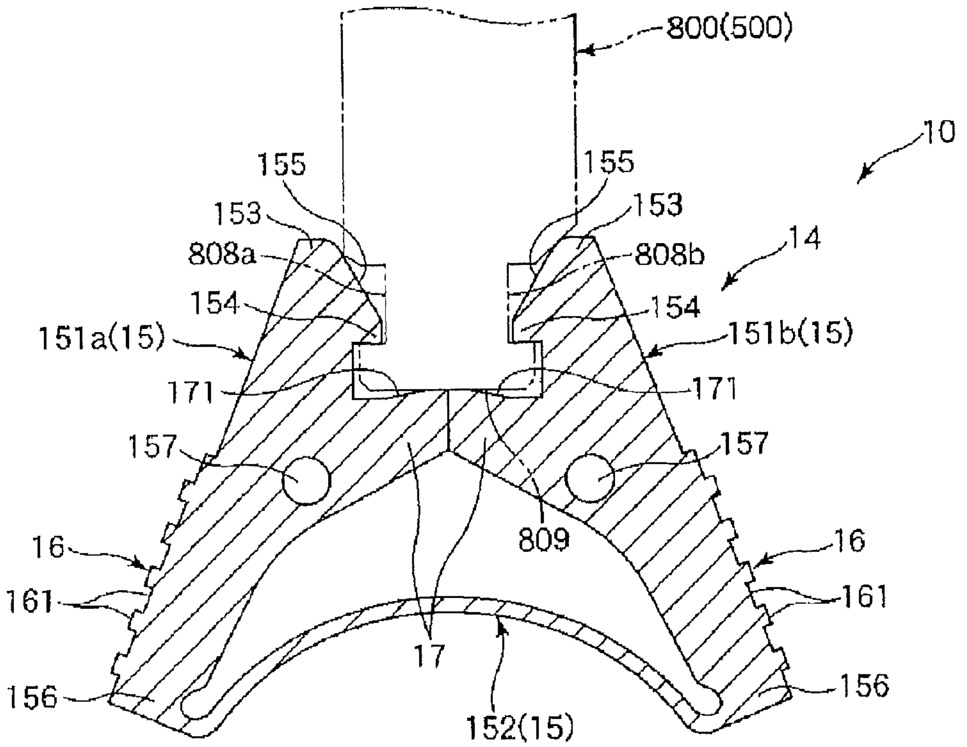
FIG. 3 is a cross-sectional view taken along the section line III-III in FIG. 1.

As shown in FIGS. 1 to 3, the connector 10 includes a connector main body 11, a first needle pipe 12*a*, a second needle pipe 12*b*, a tube-like first fitting section 13*a*, a tube-like second fitting section 13*b*, and the fixing means 14 for fixing the syringe assembly 500. The configurations of these components will be described below.

The connector main body 11 is tube-shaped, and is mounted to the first medicine container 100 and the second medicine container 200. This helps ensure that the first medicine container 100 and the second medicine container 200 are collectively held on the inside of the connector main body 11 (see FIGS. 2 and 17 to 19).

As shown in FIG. 2, the inside of a side wall 112 of the connector main body 11 is provided with a plurality of projecting engaging pieces 111. The engaging pieces 111 extend inwardly from the inner surface of the side wall 112 and engage (contact) the lower-side edge portions of the port sections 102 of the first medicine container 100 and the second medicine container 200 when the connector main body 11 is mounted to the containers. These engaging pieces 111 are disposed along the circumferential direction of the side wall of the connector main body 11 so that the engaging pieces 111 are circumferentially spaced apart from one another. With such engaging pieces 111 formed, the connector main body 11 mounted to the first medicine container 100 and the second medicine container 200 can be securely inhibited or prevented from being dismounted unwillingly.

As shown in FIGS. 1 and 2, the front side of the upper surface of a plate-shaped portion 113 of the connector main body 11 includes a pair of upstanding support plates 114 for supporting the fixing means 14. These support plates 114 are disposed opposite to each other, with a spacing therebetween. Most of the parts constituting the fixing means 14 are disposed between the support plates 114.

In addition, the first fitting section 13*a* and the second fitting section 13*b* are formed on the front side of the plate-shaped portion 113 of the connector main body 11 and project away from the plate-shaped portion 113 in a direction opposite the projecting direction of the first and second needle pipes 12*a*, 12*b*.

The first fitting section 13*a* and the second fitting section 13*b* are substantially the same in configuration. Thus the following description of the first fitting section 13*a* applies equally to the second fitting section 13*b*.

The first fitting section 13*a* is part which is tube-shaped and into which the port 603 of the first syringe 600 is to be inserted and fitted (see FIGS. 2 and 17 to 18). When the port 603 of the first syringe 600 is fitted in the first fitting section 13*a*, the inside of the first syringe 600 and the inside of the first medicine container 100 communicate with each other through the first fitting section 13*a* and the first needle pipe 12*a* (see FIG. 2).

In addition, the inner peripheral portion of the first fitting section 13*a* is provided with a tapered portion 131 in which the inside diameter gradually increases in the upward direction. The tapered portion 131 is so formed as to correspond to the port 603 of the first syringe 600, specifically, as to have a taper angle equal to that of the port 603 of the first syringe 600. This helps ensure that the first fitting section 13*a* and the port 603 of the first syringe 600 make assured fitting and, hence, these are connected in a liquid-tight manner. Consequently, when the medical solution is sucked out of the first medicine container 100 into the first syringe 600, the medical solution is prevented from leaking out via the first fitting section 13*a*.

The inner peripheral portion of the upper aperture of the first fitting section 13*a* is provided with a chamfered portion 132. This helps ensure that when the port 603 of the first syringe 600 is inserted into the first fitting section 13*a*, the port 603 is guided by the chamfered portion 132, so that the insertion is performed rather smoothly.

The second fitting section 13*b* is configured similarly to the first fitting section 13*a*. The second fitting section 13*b* is the part into which the port 603 of the second syringe 700 is inserted and fitted (see FIGS. 2 and 17 to 18). In addition, the second fitting section 13*b* has a length greater than the length of the first fitting section 13*a*.

The first fitting section 13*a* and the second fitting section 13*b* thus configured are disposed in parallel to each other, with the pair of support plates 114 of the connector main body 11 therebetween. This helps ensure that at the time of connecting the syringe assembly 500 to the connector 10, the ports 603 of the first syringe 600 and the second syringe 700 disposed in parallel to each other are fitted respectively into the first fitting section 13*a* and the second fitting section 13*b* (see FIGS. 17 and 18).

With the first fitting section 13*a* and the port 603 of the first syringe 600 fitted to each other, and with the second fitting section 13*b* and the port 603 of the second syringe 700 fitted to each other, the syringe assembly 500 is quite assuredly positioned relative to the connector main body 11. Therefore, the fixing means 14 acts on the syringe assembly 500, whereby the syringe assembly 500 can be fixed assuredly.

As shown in FIG. 2, on the back side of the top plate 113 of the connector main body 11, the first needle pipe 12*a* and the second needle pipe 12*b* are disposed respectively at positions corresponding to the first fitting section 13*a* and the second fitting section 13*b*.

The first needle pipe 12*a* and the second needle pipe 12*b* are substantially the same in configuration. The following description of the first needle pipe 12*a* thus also applies to the second needle pipe 12*b*.

The first needle pipe 12*a* projects in the opposite direction to the first fitting section 13*a*, meaning the first needle pipe 12*a* extends downwardly and the first fitting section 13*a* extends upwardly. The first needle pipe 12*a* has a sharp needle point 121 at its end, and its lumen communicates with the lumen of the first fitting section 13*a*. This helps ensure that the stopper 104 of the first medicine container 100 can be pierced by the needle point 121 of the first needle pipe 12*a*. Accordingly, the inside of the first medicine container 100 and the inside of the first syringe 600 communicate securely with each other, through the first needle pipe 12*a* and the first fitting section 13*a*.

The second needle pipe 12*b* is configured similarly to the first needle pipe 12*a*, and can pierce the stopper 104 of the second medicine container 200.

The connector 10 may be configured such that, the connector main body 11, the first needle pipe 12*a*, the second needle pipe 12*b*, the first fitting section 13*a*, and the second fitting section 13*b* are formed integrally in one piece as a single unit. Or, alternatively, the first needle pipe 12*a*, the second needle pipe 12*b*, the first fitting section 13*a*, and the second fitting section 13*b* may be configured as separate bodies, and these separate bodies may be connected to one another.

In addition, the material constituting the connector main body 11, the first needle pipe 12*a*, the second needle pipe 12*b*, the first fitting section 13*a*, and the second fitting section 13*b* is not particularly limited. For example, the various metallic materials and rigid resin materials as mentioned above in the description of the holder main body 4 can be used.

As shown in FIGS. 1 and 3, the fixing means 14 includes a lock mechanism 15, a pair of pressing pieces 16, and a pair of push-out sections 17. The lock mechanism 15 fixes the syringe assembly 500 relative to the connector main body 11 (hereinafter, the thus fixed state will be referred to as the "fixed state") when the port 603 of the first syringe 600 is fitted into the first fitting section 13*a* and the port 603 of the second syringe 700 is fitted into the second fitting section 13*b*.

As shown in FIG. 18, the lock mechanism 15 is disposed between the first fitting section 13*a* and the second fitting section 13*b*, and can fix a main body section 801 of the coupler 800 located between the first syringe 600 and the second syringe 700 to be fitted into the fitting sections. By this, the fixed state is stabilized. In addition, a fixation releasing operation for releasing the fixed state, which will be described later, can be carried out stably.

As shown in FIG. 3, the lock mechanism 15 is composed of: the pair of clamp pieces 151*a* and 151*b* which can be brought or moved toward and away from each other; and a leaf spring 152 which is an example of a biasing device which biases the clamp piece 151*a* and the clamp piece 151*b* toward each other. The spring 152 operates as a holding device configured to hold the clamp pieces 151*a*, 151*b* in engagement with the coupler 800 (the recesses 804*a*, 804*b* of the coupler) to maintain the fixed state of the connector relative to the syringe assembly.

The clamp piece 151*a* and the clamp piece 151*b* are rotatably mounted arms which are each elongated and which clamp the coupler 800 of the syringe assembly 500 between their upper end portions 153. The clamp piece 151*a* and the clamp piece 151*b* are substantially the same in configuration. Thus, the following description of the clamp piece 151*a* applies equally to the clamp piece 151*b*.

An intermediate portion of the clamp piece 151*a* is provided with a turning support section (rotation center or pivot point) 157 by which the clamp piece 151*a* is turnably or rotatably supported so as to be turnable relative to the support plates 114 of the connector main body 11. In the configuration shown in FIG. 3, the turning support section 157 is composed of a bearing in which shafts projecting from the support plates 114 are inserted.

The clamp piece 151*a* is provided, near its upper end portion 153, with the claw 154 projecting to the inner side. The claw 154 are configured to engage the recess 808*a* of the coupler 800 of the syringe assembly 500 (see FIGS. 3 and 18). The claw 154 is thus an example of an engaging part of the clamp piece or arm 151*a* that engages the coupler 800 to fix the syringe assembly in place. The syringe assembly 500 can thus be rather assuredly fixed relative to the connector main body 11, specifically the fixed state is maintained reliably. Accordingly, the syringe assembly 500 and the connector main body 11 (connector 10) can be inhibited or prevented from being disassembled unwillingly.

In addition, an inclined surface 155 is formed at an upper portion of the claw 154.

As shown in FIG. 3, the leaf spring 152 is bridgingly provided between the clamp piece 151*a* and the clamp piece 151*b*, and is curved in an arched shape. In addition, the leaf spring 152 has opposite ends supported by the lower ends 156 of the respective clamp pieces 151*a* and 151*b*. By the leaf spring 152 thus configured, the clamp piece 151*a* and the clamp piece 151*b* can be assuredly biased toward each other. This helps ensure that the claw 154 of the clamp piece 151*a* is engaged with the recess 808*a* of the coupler 800 of the syringe assembly 500, whereas the claw 154 of the clamp piece 151*b* is engaged with the recess 808*b* of the coupler 800 of the syringe 500, so that the fixed state is maintained more securely.

Thus, the connector 10 is so configured that the fixation relative to the syringe assembly 500 is performed by the lock mechanism 15. Therefore, the syringe assembly 500 can be rather assuredly connected to the connector 10, irrespective of the magnitude of a fitting force between the port 603 of the first syringe 600 and the first fitting section 13*a* or the magnitude of the fitting force between the port 603 of the second syringe 700 and the second fitting section 13*b*.

The lock mechanism 15 preferably has a structure in which the clamp pieces 151*a* and 151*b* and the leaf spring 152 are formed integrally in one piece as a single piece. This helps ensure that the lock mechanism 15 can be fairly easily produced by injection molding, for example. In addition, the number of component parts constituting the lock mechanism 15 is smaller (in this embodiment, one), as compared with the case where the clamp pieces 151*a* and 151*b* and the leaf spring 152 are configured as separate bodies.

As shown in FIGS. 1 and 3, at each of the lower ends 156 of the clamp pieces 151*a* and 151*b*, a plate-like pressing piece 16 as an operating section for performing the fixation releasing operation of releasing the fixed state is integrally formed. In addition, the clamp pieces 151*a* and 151*b* can be turned correspondingly about their turning support sections 157, by pressing the pressing pieces 16 against the biasing force of the leaf spring 152, as shown in FIG. 20. This results in the clamp piece 151*a* and the clamp piece 151*b* being spaced away from each other, and the claws 154 are disengaged correspondingly from the recesses 808*a* and 808*b* of the syringe assembly 500, so that the fixed state is released. Thus, in the connector 10, the fixed state can be assuredly released by a simple operation of pressing the pressing pieces 16.

The two arms or pressing pieces 16 are disposed symmetrically about the center line of the connector main body 11. Specifically, they are arranged between the first fitting section 13*a* and the second fitting section 13*b*, and in the direction orthogonal to the layout direction of these fitting sections (i.e., the two pressing pieces 16 are arranged orthogonal to a plane containing the central axis of the first fitting section 13*a* and the central axis of the second fitting section 13*b*). Stated differently, the rotation or pivot axes 157 about which the arms 16 rotate are parallel to one another and parallel to the plane containing the central axes of the fittings 13*a*, 13*b*. This helps ensure that the fixation releasing operation can be carried out relatively stably.

In addition, each of the pressing pieces 16 is formed with a multiplicity of recesses and projections 161. This helps ensure that when the pressing pieces 16 are pressed with fingers, the fingers can be securely inhibited or prevented from slipping on the pressing pieces 16.

As shown in FIGS. 3 and 20, the clamp pieces 151*a* and 151*b* are provided with the push-out sections 17 at intermediate portions in the longitudinal directions of the clamp pieces, specifically at their portions on the upper side relative to the turning support sections 157. As shown in FIG. 20, each of the push-out sections 17 is a part which pushes the syringe assembly 500 upward in an interlocked manner with the fixation releasing operation when the fixation releasing operation is performed by pressing each of the clamp pieces 16 so that the syringe assembly 500 is pushed upward whenever the fixation releasing operation is performed.

The two push-out sections 17 are substantially the same in configuration. The following description of the push-out section 17 on the clamp piece 151*a* side thus applies equally to the push-out section 17 on the other clamp piece 151*b* side.

The push-out section 17 is composed of a projection which projects to the inner side of the clamp piece 151*a*. That is, the push-out section 17 projects away from the clamp piece 151*a* and toward the push-out section 17 of the other clamp piece 151*b*. The upper surface of the projecting push-out section 17 constitutes a contact surface 171 which is vertically below the engaging part 154 and which makes contact with a leading end surface 809 of the coupler 800 (main body section 801) of the syringe assembly 500 in the fixed state (see FIG. 3 and FIG. 20(*a*)). When the fixation releasing operation is performed, the contact surface 171 is turned about the turning support section 157 to move upward, thereby pressing upward the leading end surface 809 of the coupler 800 (see FIG. 20*b*)). In this instance, the syringe assembly 500 as a whole is moved upward. Therefore, the port 603 of the first syringe 600 is pulled off or separated from the first fitting section 13*a*, so that the fitting between these members is released. Simultaneously, the port 603 of the second syringe 700 is pulled off or separated from the second fitting section 13*b*, so that the fitting between these members is also released.

Thus, the connector 10 is so configured as to push out the syringe assembly 500 connected to the connector 10. Accordingly, the syringe assembly 500 in the connected state can be disconnected relatively easily and assuredly, irrespective of the magnitude of the fitting force between the port 603 of the first syringe 600 and the first fitting section 13*a* or the magnitude of the fitting force between the port 603 of the second syringe 700 and the second fitting section 13*b*.

In addition, after the syringe assembly 500 is disconnected, removal of the pressures exerted on the pressing pieces 16 causes the shape of the leaf spring 152 to be restored, so that the clamp pieces 151*a* and 151*b* are again brought close to each other as shown in FIG. 20(*c*).

Because the contact surfaces 171 of the push-out sections 17 are already in contact with the leading end surface 809 of the coupler 800 of the syringe assembly 500 in the fixed state as above-mentioned, the releasing of the fixed state and the pushing-out by the contact surfaces 171 are performed substantially simultaneously. Specifically, when the releasing of the fixed state is conducted, the pushing of the leading end surface 809 by the contact surfaces 171 is carried out rather swiftly. This helps ensure that the syringe assembly 500 connected to the connector 10 can be disconnected rather speedily. Examples of ways of providing a configuration in which the releasing of the fixed state and the pushing-out are performed concurrently as above-mentioned include a manner in which the positions or shapes of the claws 154 and the push-out sections 17, the positions of the turning support sections 157, or the like are appropriately set.

In addition, the material constituting the components of the fixing means 14 is not specifically restricted. For example, the various metallic materials and rigid resin materials discussed above in the description of the holder main body 4 can be used to fabricate the fixing means.

Now, one examples of the method of using the connector 10 will be described in detail below.

[1] First, the holder 2 with the first medicine container 100, the second medicine container 200, the first liquid container 300 and the second liquid container 400 contained therein (in the state shown in FIG. 4), the connector for mixing 3 in an unused state (the state shown in FIG. 9), the connector 10, and the syringe assembly 500 are prepared. The holder 2 is mounted on a support base such as a table. In addition, the syringe 500 has the first syringe 600 and the second syringe 700 in the state in which the plungers 602 are retracted most (the state shown in FIG. 17).

[2] With the connector for mixing 3 in the state shown in FIG. 9, the liquid-side cap 9*a* provided with numeral "1" as the mark 911 is detached (see FIG. 12) from the remainder of the connector for mixing 3. The detaching operation can be carried out by nipping or grasping the tab 93 of the liquid-side cap 9*a* with fingers or the like.

[3] Next, the connector for mixing 3 from which the liquid-side cap 9*a* has been detached is inserted from above toward the liquid-side containing section 45 of the holder 2 (holder main body 4) mounted on the support base, from the side of the liquid-side tube-shaped section 82 (liquid-side needle 71) as shown in FIG. 12. This results in the connecting operation of the connector for mixing 3 with the first liquid container 300 and the second liquid container 400, and therefore the liquid container connecting operation, being performed properly. As mentioned above, the liquid-side needle 71 of the first double-pointed needle 7*a* of the connector for mixing 3 pierces the stopper 104 of the first liquid container 300, whereas the liquid-side needle 71 of the second double-pointed needle 7*b* pierces the stopper 104 of the second liquid container 400.

[4] Subsequently, the medicine-side tube-shaped section 83 of the connector for mixing 3 in the state shown in FIG. 12 is gripped, and the first liquid container 300 and the second liquid container 400 are taken out of the holder 2 together with the connector for mixing 3 (see FIG. 13).

[5] Next, from the connector for mixing 3 in the state shown in FIG. 13, the medicine-side cap 9*b* provided with numeral "2" as the mark 911 is detached as illustrated in FIG. 14. The detaching operation can be carried out by nipping or grabbing the tab 93 of the medicine-side cap 9*b* with fingers or the like.

[6] Subsequently, the connector for mixing 3 from which the medicine-side cap 9*b* has been detached is inverted upside down. Then, speedily, the connector for mixing 3 is inserted from above toward the medicine-side containing section 44 of the holder 2, from the side of the medicine-side tube-like section 83 (medicine-side needle 72) as depicted in FIG. 14. This results in the connector for mixing 3 and the first medicine container 100 as well as the second medicine container 200 being connected, and therefore, the liquid container connecting operation is performed properly. In this instance, as above-mentioned, the medicine-side needle 72 of the first double-pointed needle 7*a* of the connector for mixing 3 pierces the stopper 104 of the first medicine container 100, whereas the medicine-side needle 72 of the second double-pointed needle 7*b* is in the state of piercing the stopper 104 of the second medicine container 200. Consequently, the first liquid container 300 and the first medicine container 100 are interconnected assuredly, whereas the second liquid container 400 and the second medicine container 200 are interconnected relatively assuredly through the connector for mixing 3

Since the inside of the first medicine container 100 and the inside of the second medicine container 200 are set at negative pressures, the liquid inside the first liquid container 300 is drawn toward the first medicine container 100 side, and flows through the first double-pointed needle 7*a* into the first medicine container 100. Similarly, the liquid inside the second liquid container 400 is drawn toward the second medicine container 200 side, and flows through the second double-pointed needle 7*b* into the second medicine container 200.

[7] Next, the liquid-side tube-like section 82 of the connector for mixing 3 in the state shown in FIG. 14 is gripped, and the first medicine container 100 and the second medicine container 200 are taken out of or removed from the holder 2 together with the connector for mixing 3 (see FIG. 15).

[8] Subsequently, the connector for mixing 3 is shaken a few times. This helps ensure that the medicine inside the first medicine container 100 and the medicine inside the second medicine container 200 are diluted with or dissolved in the liquid flowing in, with the result that the medical solutions are contained correspondingly in the first medicine container 100 and the second medicine container 200.

Figure 16:
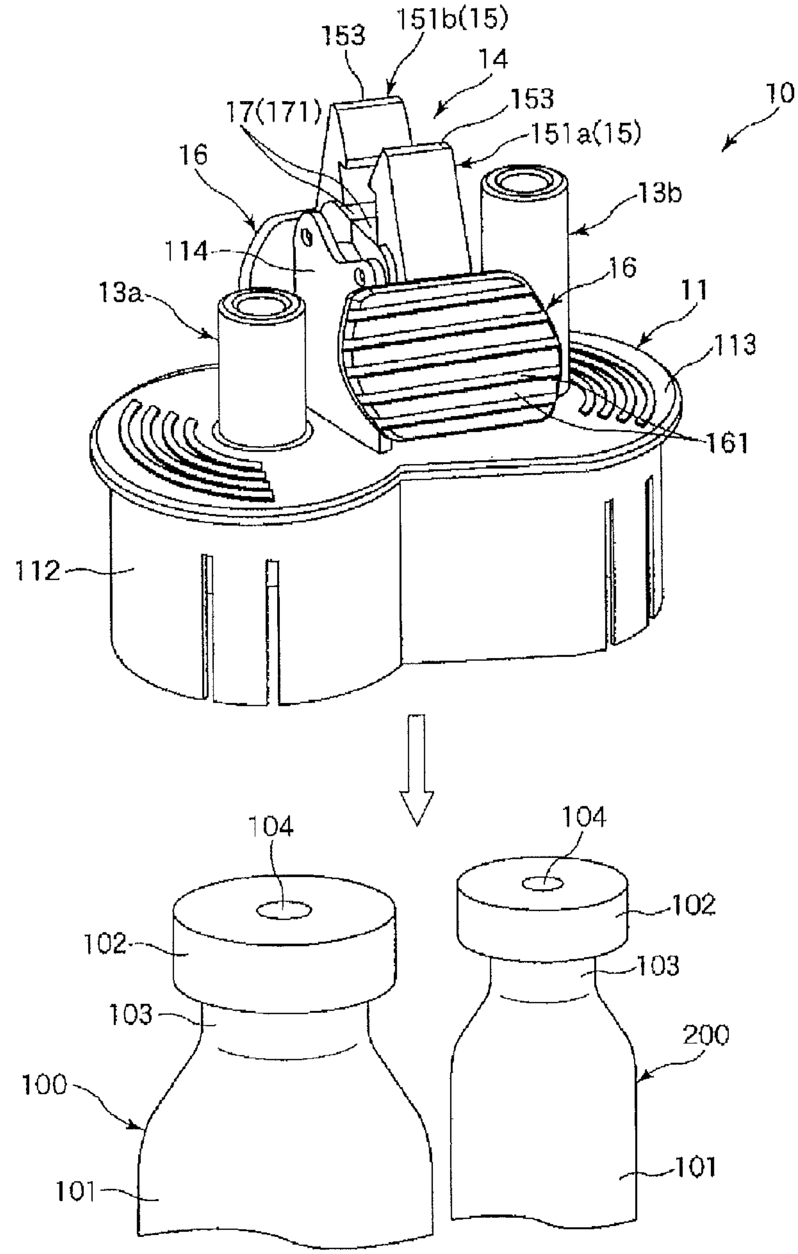
FIG. 16 is a view for describing sequentially the method of using the connector shown in FIG. 1.

[9] Next, the connector for mixing 3 is detached from the first medicine container 100 and the second medicine container 200 as illustrated in FIG. 16. While the stoppers 104 of the first medicine container 100 and the second medicine container 200 are exposed in this instance in the configuration shown in FIG. 16, detachable rubber caps for covering the stoppers 104 may be put on the stoppers 104. This helps prevent fingers or the like from making contact with the stoppers 104 unwillingly, thereby maintaining a sterile state of the stoppers 104. The member used to cover the stopper 104 is not limited to the rubber cap. for example, a rubber membrane or a film may also be used.

[10] Subsequently, as shown in FIG. 16, the connector 10 is mounted to the first medicine container 100 and the second medicine container 200 from which the connector for mixing 3 has been detached. In the case where the rubber caps are put on in the above-mentioned operation [9], the rubber caps are removed before mounting the connector 10.

As a result of the mounting of the connector 10, the first needle pipe 12*a* pierces the stopper 104 of the first medicine container 100, and the second needle pipe 12*b* pierces the stopper 104 of the second medicine container 200.

[11] In the condition where the connector 10 mounted to the first medicine container 100 and the second medicine container 200 are kept oriented upward, specifically in the condition where the connector 10 is located above the first medicine container 100 and the second medicine container 200, the syringe assembly 500 is connected to the connector 10 as shown in FIG. 17. At the time of performing this connection, the first syringe 600 of the syringe assembly 500 corresponds to the first fitting section 13*a* of the connector 10, whereas the second syringe 700 corresponds to the second fitting section 13*b* of the connector 10. Then, in the condition where the syringes and the fitting sections are thus made to correspond, the syringe assembly 500 is pushed into the connector 10. This helps ensure that the leading end section of the coupler 800 of the syringe assembly 500 outwardly pushes the clamp pieces 151*a* and 151*b* while sliding along the inclined surfaces 155 of the claws 154 of the clamp pieces 151*a* and 151*b*. Then, when the leading end section of the coupler 800 rides over the claws 154, the claws 154 enter into and engage with the recesses 808*a* and 808*b* of the coupler 800, correspondingly. This results in the fixed state. In the fixed state, the port 603 of the first syringe 600 is fitted in the first fitting section 13*a*, and the port 603 of the second syringe 700 is fitted in the second fitting section 13*b*. This results in that the inside of the first syringe 600 and the inside of the first medicine container 100 communicate with each other, whereas the inside of the second syringe 700 and the inside of the second medicine container 200 communicate with each other, through the connector 10.

[12] Next, the operating section 802 of the syringe assembly 500 is gripped, and the plungers 602 of the first syringe 600 and the second syringe 700 are collectively pulled together with the operating section 802 (see FIG. 18). This results in the medical solution inside the first medicine container 100 being loaded into the first syringe 600, and the medical solution inside the second medicine container 200 being loaded into the second syringe 700. The operation of pulling the plungers 602 may be performed by inverting the state shown in FIG. 12 upside down.

In addition, after the first syringe 600 and the second syringe 700 are loaded correspondingly with the medical solutions, an operation of pressing the operating section 802 of the syringe assembly 500 to remove air present in the syringes is preferably performed.

[13] Subsequently, the pressing pieces 16 of the connector 10 are pressed, whereby the syringe assembly 500 is disconnected from the connector 10 as above-mentioned (see FIG. 19). Then, the syringe assembly 500 can be used, for example, as an applicator for mixing the medical solutions and applying the mixed solution to a living body.

While the connector disclosed here has been described referring to the embodiment shown in the drawings, the disclosure is not limited to the embodiment, and each of the components of the connector can be replaced by different components exhibiting a similar or equivalent function. And additional features and components may be added.

The syringe assembly connected to the connector in the described embodiment has two syringes, but this configuration is not limitative. A syringe assembly having only one syringe or having three or more syringes may also be adopted.

The disclosed connector is not limited to use in loading a medical solution from a medicine container preliminarily filled with the solution into an empty syringe. The connector can also be used, for example, in loading a medical solution from a syringe preliminarily filled with the medical solution into an empty medicine container.

The detailed description above describes features and aspects of an embodiment of a connector disclosed by way of example. The invention is not limited, however, to the precise embodiment and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A mixing connector connectable to a medicine container, which contains medicine and which is positioned in a first port of a holder, and a liquid container, which contains liquid different from the medicine and which is positioned in a second port of the holder possessing a configuration different from a configuration of the first port, the mixing connector comprising:

a support section;

a double-pointed needle supported in the support section and extending over a longitudinal extent, the double-pointed needle including a first portion projecting away from the support section in a first projecting direction and terminating at a first sharpened end for puncturing a stopper in the medicine container, the double-pointed needle including a second portion projecting away from the support section in a second projecting direction and terminating at a second sharpened end for puncturing a stopper in the liquid container, the double-pointed needle possessing a lumen extending throughout the longitudinal extent of the double-pointed needle and opening to both the first sharpened end and the second sharpened end of the double-pointed needle;

a first tube-shaped section fixed to the support section and projecting away from the support section in the first projecting direction, the first tube-shaped section possessing an inner peripheral surface and the first portion of the double-pointed needle possessing an outer peripheral surface, the first tube-shaped section surrounding the first portion of the double-pointed needle so that a space exists between the outer peripheral surface of the first portion of the double-pointed needle and the inner peripheral surface of the first tube-shaped section;

a second tube-shaped section fixed to the support section and projecting away from the support section in the second projecting direction, the second tube-shaped section possessing an inner peripheral surface and the second portion of the double-pointed needle possessing an outer peripheral surface, the second tube-shaped section surrounding the second portion of the double-pointed needle so that a space exists between the outer peripheral surface of the second portion of the double-pointed needle and the inner peripheral surface of the second tube-shaped section;

the first tube-shaped section and the second tube-shaped section each possessing an outer periphery, the outer periphery of the first tube-shaped section and the second tube-shaped section being differently shaped;

the shape of the outer periphery of the first tube-shaped section permitting the first tube-shaped section to be positioned in the first port of the holder and preventing the first tube-shaped section from being positioned in the second port of the holder; and the shape of the outer periphery of the second tube-shaped section permitting the second tube-shaped section to be positioned in the second port of the holder and preventing the second tube-shaped section from being positioned in the first port of the holder.

2. The connector according to claim 1, further comprising a removable first cap covering an open end of the first tube-shaped section to enclose an interior of the first tube-shaped section in which the first portion of the double-pointed needle is located, and a removable second cap covering an open end of the second tube-shaped section to enclose an interior of the second tube-shaped section in which the second portion of the double-pointed needle is located.

3. The connector according to claim 1, wherein the double-pointed needle is a first double-pointed needle, and further comprising:

a second double-pointed needle supported in the support section and extending over a longitudinal extent, the second double-pointed needle including a first portion projecting away from the support section in the first projecting direction and terminating at a first sharpened end, the second double-pointed needle including a second portion projecting away from the support section in the second projecting direction and terminating at a second sharpened end, the second double-pointed needle possessing a lumen extending throughout the longitudinal extent of the second double-pointed needle and opening to both the first sharpened end and the second sharpened end of the second double-pointed needle;

the first and second portions of the second double-pointed needle possessing an outer peripheral surface;

the first tube-shaped section surrounding the first portion of the second double-pointed needle so that a space exists between the outer peripheral surface of the first portion of the second double-pointed needle and the inner peripheral surface of the first tube-shaped section;

the second tube-shaped section surrounding the second portion of the second double-pointed needle so that a space exists between the outer peripheral surface of the second portion of the second double-pointed needle and the inner peripheral surface of the second tube-shaped section.

4. A syringe assembly in combination with a connector, the syringe assembly comprising:

a syringe that includes a plunger slidably positioned in an outer cylinder, a tube-shaped port protruding from a leading end of the outer cylinder, and a holder fixed to the syringe, the holder including an engagement portion;

the connector comprising:

a connector main body configured to be mounted on a medical solution container containing a medical solution;

a needle pipe projecting in a first projecting direction from the connector main body, the needle pipe possessing a sharp needle point at an end of the needle pipe remote from the connector main body, the needle pipe including a lumen opening to the sharp needle point;

a tube-shaped fitting protruding from the connector main body in a second projecting direction opposite the first projecting direction, the tube-shaped fitting possessing an interior sized and shaped to receive the tube-shaped port of the syringe, the interior of the tube-shaped fitting communicating with the lumen of the needle pipe;

an arm rotatably mounted on the connector main body to engage the engagement portion of the holder to fix the syringe assembly in place relative to the connector with the tube-shaped port of the syringe positioned in the tube-shaped fitting of the connector; and a holding device connected to the arm to hold the arm in engagement with the engagement portion of the holder and to permit the arm to be moved out of engagement with the engagement portion of the holder to permit the syringe assembly to be released from the connector.

5. The combination according to claim 4, wherein the arm is a first arm rotatably mounted on the connector main body to rotate about a first pivot axis, and including a second arm rotatably mounted on the connector main body to rotate about a second pivot axis spaced from the first pivot axis, the engagement portion of the holder being a first groove engaged by the first arm, the holder including a second groove engaged by the second arm.

6. The connector according to claim 4, wherein the syringe is a first syringe, the outer cylinder is a first outer cylinder, the plunger is a first plunger, the tube-shaped fitting is a first tube-shaped fitting, and the needle pipe is a first needle pipe;

the syringe assembly comprising:

a second syringe, the second syringe including a second plunger slidably positioned in a second outer cylinder, a second tube-shaped port protruding from a leading end of the second outer cylinder, and the holder fixing the first and second syringes in place relative to each other;

the connector comprising:

a second needle pipe projecting from the connector main body parallel to the first needle pipe, the second needle pipe possessing a sharp needle point at an end of the second needle pipe remote from the connector main body, the second needle pipe including a lumen opening to the sharp needle point of the second needle pipe;

a second tube-shaped fitting protruding from the connector main body parallel to the first tube-shaped fitting, the second tube-shaped fitting possessing an interior sized and shaped to receive the second tube-shaped port of the syringe, the interior of the second tube-shaped fitting communicating with the lumen of the second needle pipe.

7. The combination according to claim 6, wherein the syringe assembly includes a coupler connected to both the first and second plungers, the coupler being movable relative to the holder and the first and second outer cylinders to move the first and second plungers simultaneously.

8. The combination according to claim 4, wherein the holding device is a spring connected to the first arm.

* * * * *